United States Patent
Vera Valdes et al.

(10) Patent No.: US 10,279,009 B2
(45) Date of Patent: May 7, 2019

(54) HISTONE DEACETYLASE (HDAC) INHIBITOR UP-REGULATES CAR EXPRESSION AND TARGETED ANTIGEN INTENSITY, INCREASING ANTITUMOR EFFICACY

(71) Applicant: Baylor College of Medicine, Houston, TX (US)

(72) Inventors: Juan Fernando Vera Valdes, Bellaire, TX (US); Malcolm Brenner, Bellaire, TX (US); Usanarat Anurathapan, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 512 days.

(21) Appl. No.: 14/335,766

(22) Filed: Jul. 18, 2014

(65) Prior Publication Data

US 2015/0023937 A1 Jan. 22, 2015

Related U.S. Application Data

(60) Provisional application No. 61/847,957, filed on Jul. 18, 2013.

(51) Int. Cl.
| | | |
|---|---|---|
| *A61K 39/395* | (2006.01) | |
| *A61K 38/17* | (2006.01) | |
| *A61K 31/706* | (2006.01) | |
| *A61K 35/17* | (2015.01) | |
| *C12N 5/0783* | (2010.01) | |
| *A61K 45/06* | (2006.01) | |
| *A61K 38/16* | (2006.01) | |

(52) U.S. Cl.
CPC .......... *A61K 38/177* (2013.01); *A61K 31/706* (2013.01); *A61K 35/17* (2013.01); *A61K 38/164* (2013.01); *A61K 45/06* (2013.01); *C12N 5/0638* (2013.01); *C12N 2501/06* (2013.01); *C12N 2501/065* (2013.01); *C12N 2510/00* (2013.01)

(58) Field of Classification Search
None
See application file for complete search history.

(56) References Cited

U.S. PATENT DOCUMENTS

2014/0271582 A1   9/2014   Foreman et al.

FOREIGN PATENT DOCUMENTS

| JP | 2011/522814 A | 8/2011 |
|---|---|---|
| WO | 2009150405 A1 | 12/2009 |
| WO | 2013/050596 A1 | 4/2013 |

OTHER PUBLICATIONS

Carl Jun. et al. Nat Rev Immuno. 2009, 9(10) 704-716.*
Lal et al., Journal of Immunology, 2009, vol. 182, pp. 259-273.*
Jager et al., "Inverse relationship of melanocyte differentiation antigen expression in melanoma tissues and CD8+ cytotoxic-T-cell responses: evidence for immunoselection of antigen-loss variants in vivo," Int J Cancer 1996, vol. 66, pp. 470-476.
Riker et al., "Immune selection after antigen-specific immunotherapy of melanoma," Surgery 1999, vol. 126, pp. 112-120.
Wente et al., "Prostate stem cell antigen is a putative target for immunotherapy in pancreatic cancer", Pancreas 2005, vol. 31, pp. 119-125.
Mihara et al., "Synergistic and persistent effect of T-cell immunotherapy with anti-CD19 or anti-CD38 chimeric receptor in conjunction with rituximab on B-cell non-Hodgkin lymphoma", Br J Haematol 2010, vol. 151, pp. 37-46.
Kloss et al., "Combinatorial antigen recognition with balanced signaling promotes selective tumor eradication by engineered T cells", Nat Biotechnol 2013, vol. 31, pp. 71-75.
Wilkie et al., "Dual targeting of ErbB2 and MUC1 in breast cancer using chimeric antigen receptors engineered to provide complementary signaling", J Clin Immunol 2012, vol. 32, pp. 1059-1070.
Porter et al., "Chimeric antigen receptor-modified T cells in chronic lymphoid leukemia", N Engl J Med 2011; vol. 365, pp. 725-733.
Kochenderfer et al., "B-cell depletion and remissions of malignancy along with cytokine-associated toxicity in a clinical trial of anti-CD19 chimeric-antigen-receptor-transduced", T cells. Blood 2012, vol. 119, pp. 2709-2720.
Pule et al., "Virus-specific T cells engineered to coexpress tumor-specific receptors: persistence and antitumor activity in individuals with neuroblastoma", Nat Med 2008, vol. 14, pp. 1264-1270.
Till et al., "Adoptive immunotherapy for indolent non-Hodgkin lymphoma and mantle cell lymphoma using genetically modified autologous CD20-specific T cells", Blood 2008, vol. 112, pp. 2261-2271.
Jensen et al., "Antitransgene rejection responses contribute to attenuated persistence of adoptively transferred CD20/CD19-specific chimeric antigen receptor redirected T cells in humans", Biol Blood Marrow Transplant 2010, vol. 16, pp. 1245-1256.
Brentjens et al., "CD19-Targeted T Cells Rapidly Induce Molecular Remissions in Adults with Chemotherapy-Refractory Acute Lymphoblastic Leukemia", Sci Transl Med 2013, vol. 5, 177ra38.
Grupp et al., "Chimeric Antigen Receptor-Modified T Cells for Acute Lymphoid Leukemia", N Engl J Med 2013, vol. 368, pp. 1509-1518.
Chhieng et al., "MUC1 and MUC2 expression in pancreatic ductal carcinoma obtained by fine-needle aspiration", Cancer 2003, vol. 99, pp. 365-371.

(Continued)

*Primary Examiner* — Yunsoo Kim
(74) *Attorney, Agent, or Firm* — Norton Rose Fulbright US LLP

(57) ABSTRACT

Embodiments of the invention employ methods and compositions for enhancing potency of immune cells that express one or more therapeutic proteins. In certain cases, the methods modulate expression of a CAR transgene in an immune cell, such as a T cell. Specific embodiments employ the exposure of cells and/or individuals to be treated with the cells with an effective amount of at least one agent that upregulates expression of the therapeutic protein, such as a mitogen, histone deacetylase inhibitor, and or DNA methyltransferase inhibitor.

15 Claims, 36 Drawing Sheets

(56) References Cited

OTHER PUBLICATIONS

Lau et al., "Differential expression of MUC1, MUC2, and MUC5AC in carcinomas of various sites: an immunohistochemical study", Am J Clin Pathol 2004, vol. 122, pp. 61-69.
James et al., "Antibody-mediated B-cell depletion before adoptive immunotherapy with T cells expressing CD20-specific chimeric T-cell receptors facilitates eradication of leukemia in immunocompetent mice", Blood 2009, vol. 114, pp. 5454-5463.
Sanchez et al., "Combining T-cell immunotherapy and anti-androgen therapy for prostate cancer", Prostate Cancer Prostatic Dis 2013, vol. 16, pp. 123-131.
Katari et al., "Engineered T cells for pancreatic cancer treatment", HPB (Oxford) 2011, vol. 13, pp. 643-650.
Nakazawa et al., "PiggyBac-mediated cancer immunotherapy using EBV-specific cytotoxic T-cells expressing HER2-specific chimeric antigen receptor," Mol Ther 2011, vol. 19, pp. 2133-2143.
Reiter et al., "Prostate stem cell antigen: a cell surface marker overexpressed in prostate cancer", Proc Natl Acad Sci U S A 1998, vol. 95, pp. 1735-1740.
Spicer et al., "Molecular cloning and analysis of the mouse homologue of the tumor-associated mucin, MUC1, reveals conservation of potential O-glycosylation sites, transmembrane, and cytoplasmic domains and a loss of minisatellite-like polymorphism", J Biol Chem 1991, vol. 266, pp. 15099-15109.
Vera et al., "Accelerated production of antigen-specific T cells for preclinical and clinical applications using gas-permeable rapid expansion cultureware (G-Rex)", J Immunother 2010, vol. 33, pp. 305-315.
Sato et al., "Discovery of novel targets for aberrant methylation in pancreatic carcinoma using high-throughput microarrays", Cancer Res 2003, vol. 63, pp. 3735-3742.
Savoldo et al., "CD28 costimulation improves expansion and persistence of chimeric antigen receptor-modified T cells in lymphoma patients", J Clin Invest 2011, vol. 121, pp. 1822-1826.
Till et al., "CD20-specific adoptive immunotherapy for lymphoma using a chimeric antigen receptor with both CD28 and 4-1BB domains: pilot clinical trial results", Blood 2012, vol. 119, pp. 3940-3950.
Louis et al., "Antitumor activity and long-term fate of chimeric antigen receptor-positive T cells in patients with neuroblastoma", Blood 2011, vol. 118, pp. 6050-6056.
Kalos et al., "T cells with chimeric antigen receptors have potent antitumor effects and can establish memory in patients with advanced leukemia", Sci Transl Med 2011, vol. 3, 95ra73.
Porter et al., "Chimeric Antigen Receptor T Cells Directed Against CD19 Induce Durable Responses and Transient Cytokine Release Syndrome in Relapsed, Refractory CLL and ALL", Blood (Ash Annual Meeting Abstracts) 2012, 120 (21), No. 717.
Bollard et al., "Complete responses of relapsed lymphoma following genetic modification of tumor-antigen presenting cells and T-lymphocyte transfer", Blood 2007, vol. 110, pp. 2838-2845.
Cruz et al., "Improving T-cell therapy for relapsed EBV-negative Hodgkin lymphoma by targeting upregulated MAGE-A4", Clin Cancer Res 2011, vol. 17, pp. 7058-7066.
Goodyear et al., "Induction of a CD8+ T-cell response to the MAGE cancer testis antigen by combined treatment with azacitidine and sodium valproate in patients with acute myeloid leukemia and myelodysplasia", Blood 2010, vol. 116, pp. 1908-1918.
Brossart et al., "Induction of cytotoxic T-lymphocyte responses in vivo after vaccinations with peptide-pulsed dendritic cells", Blood 2000, vol. 96, pp. 3102-3108.
Lamers et al., "Treatment of metastatic renal cell carcinoma with autologous T-lymphocytes genetically retargeted against carbonic anhydrase IX: first clinical experience", J Clin Oncol 2006, vol. 24, pp. e20-e22.
Morgan et al., "Case report of a serious adverse event following the administration of T cells transduced with a chimeric antigen receptor recognizing ERBB2", Mol Ther 2010, vol. 18, pp. 843-851.
Di Stasi et al., "Inducible apoptosis as a safety switch for adoptive cell therapy", N Engl J Med 2011, vol. 365, pp. 1673-1683.
Berger et al., "Analysis of transgene-specific immune responses that limit the in vivo persistence of adoptively transferred HSV-TK-modified donor T cells after allogeneic hematopoietic cell transplantation", Blood 2006, vol. 107, pp. 2294-2302.
Kohlgraf et al., "Contribution of the MUC1 tandem repeat and cytoplasmic tail to invasive and metastatic properties of a pancreatic cancer cell line", Cancer Res 2003, vol. 63, pp. 5011-5020.
Yang et al., "Murine six-transmembrane epithelial antigen of the prostate, prostate stem cell antigen, and prostate-specific membrane antigen: prostate-specific cell-surface antigens highly expressed in prostate cancer of transgenic adenocarcinoma mouse prostate mice", Cancer Res. 2001, vol. 61, pp. 5857-5860.
Song et al., "Upregulation of NKG2D Ligands by Sodium Valproate (VPA) Increased the Susceptibility of Cancer Cells That Are Recognized by Chimeric NKG2D-4-1 BB-CD3z T Cells", Molecular Therapy; 15th Annual Meeting of the American-Society-of-Gene-and-Cell-Therapy (ASGCT); May 16-19, 2012, vol. 20, No. Suppl. 1, May 1, 2012, p. S77, Academic Press, Philadelphia, PA, USA.
Chu et al., "Effectively targeting sensitive and resistant Burkitt lymphoma by anti-CD20 chimeric antigen receptor (CAR) modified expanded natural killer (NK) cells combined with a histone deacetylase inhibitor, romidepsin", Bone Marrow Transplantation; 39th Annual Meeting of the European-Group-for-Blood-and-Marrow-Transplantation (EBMT); London, UK; Apr. 7-10, 2013, vol. 48, No. Suppl. 2, Apr. 1, 2013 (Apr. 1, 2013), p. S15 Nature Publishing Group, GB.
Anurathapan et al., "Rapid Assessment of T-Cell Function in an Animal-Free Model—The Artificial-Mouse Model", Molecular Therapy, vol. 21, No. Suppl. 1, Jun. 2013 (Jun. 2013), p. S237, & 16th Annual Meeting of the American-Society-of-Gene-and-Cell-Therapy (ASGCT); Salt Lake City, UT, USA; May 15-18, 2013.
Dotti et al., "Review Fifteen Years of Gene Therapy Based on Chimeric Antigen Receptors: "Are We Nearly There Yet?"", Human Gene Therapy, Nov. 1, 2009, No. 20, pp. 1229-1239.
Guo, at al; "DeNovo Induction of a Cancer/Testis Antigen by 5-Aza-2'-Deoxycytidine augments Adoptive Immunotherapy in a Murine Tumor Model" Am. Assoc. of Cancer Research, 2006; 66: (2); Jan. 15, 2006.
Molecular Therapy, May 2012, vol. 12, Suppl.1, p. S77, No. 196.
Bone marrow transplantation, Apr. 2013, vol. 48, Suppl.2, p. S15, No. O150.

* cited by examiner

B

HISTONE DEACETYLASE (HDAC) INHIBITOR UP-REGULATES CAR EXPRESSION AND TARGETED ANTIGEN INTENSITY, INCREASING ANTITUMOR EFFICACY

This application claims priority to U.S. Provisional Patent Application Ser. No. 61/847,957, filed Jul. 18, 2013, which application is incorporated by reference herein in its entirety.

This invention was made with government support under W81XWH-11-1-0625 awarded by the Department of Defense Prostate Cancer Research Program and CA094237 and P50 CA058183 awarded by the NIH. The government has certain rights in the invention.

TECHNICAL FIELD

The field of the present invention includes at least the fields of cell biology, molecular biology, immunology, and/or medicine, including cancer medicine.

BACKGROUND

T cells modified to express tumor-directed chimeric antigen receptors (CARs) have shown clinical efficacy in treating both hematological malignancies and solid tumors. It is likely, however, that the most effective use of CAR-modified T cells will require additional engineering to enable them to overcome tumor immune escape mechanisms. One of these escape strategies is target antigen modulation under selective pressure. This phenomenon has been reported as a cause of failure in both preclinical and clinical studies using adoptively-transferred T cells with single antigen specificity to treat heterogeneous tumors.

SUMMARY

The methods and compositions provided herein address the potential problem of target antigen modulation, e.g., reduction of target cancer antigen expression, under selective pressure, e.g., during chemotherapy, by providing methods and compositions effective to circumvent such modulation. The methods and compositions herein utilize one or more agents that upregulate expression of a therapeutic protein, e.g., a chimeric antigen receptor (CAR), in an immune cell, e.g., T lymphocyte, such that the cell maintains efficacy as a therapeutic even when target antigen expression is reduced by selective pressure. In certain embodiments, the expression of the therapeutic protein is upregulated by the agent in a sufficient amount to allow the immune cell to be or remain therapeutically effective. In specific embodiments, the expression is upregulated in the cell by the agent to a level that is greater than that in a cell that is not exposed to the agent.

In one aspect, provided herein is a method of enhancing potency, e.g., cancer cell-killing activity, of immune cells that express at least one therapeutic protein, by exposing one or more agents to such immune cells such that expression of said at least one therapeutic protein therein is upregulated or increased compared to such immune cells that are not exposed to the one or more agents. In certain embodiments, provided herein is a method of increasing the cancer cell-killing activity of a population of immune cells that express a therapeutic protein, e.g., a CAR, comprising contacting the immune cells with one or more agents for a time and in an amount sufficient to increase expression of the therapeutic protein. In certain embodiments, provided herein is a method of increasing cancer cell-killing activity of a population of immune cells that express a therapeutic protein, e.g., a CAR, comprising contacting the immune cells with one or more agents for a time and in an amount sufficient to increase expression of the therapeutic protein and thereby increase the cancer cell-killing activity of the population of immune cells. In specific embodiments, the upregulation or increase in expression is detectable by standard means, such as by western blotting or Northern blotting, for example.

In particular embodiments, the population of immune cells is contacted with one or more agents to upregulate expression of the therapeutic protein when the cells are in vitro, ex vivo, and/or in vivo. In one embodiment, the population of immune cells is contacted with the one or more agents an individual who has been administered, or is to be administered, the immune cells. In specific embodiments, the immune cells are contacted with the one or more agents prior to administration of the immune cells to the individual, or the immune cells are contacted with the one or more agents after administration of the immune cells to the individual. In a specific embodiment, the method comprises isolating immune cells lacking the therapeutic protein from an individual; engineering the immune cells to express the therapeutic protein; administering the engineered immune cells to the same individual; and subsequently administering the agent to the individual in an amount sufficient to cause an increase in the expression of the therapeutic protein in the immune cells. Immune cells from the individual may be obtained at or near the time of therapy or may have been suitably stored prior to therapy.

In certain embodiments, therapeutic protein-expressing immune cells to be delivered to an individual are obtained from one or more other individuals. Such cells may be assayed and/or manipulated such that they are safe to be delivered to another individual and are less likely to be rejected by the recipient individual's own immune system, for example. The cells may be stored in a repository, for example.

In specific embodiments of any of the embodiments herein, the agent comprises one or more of an epigenetic modifier and/or a mitogen. In particular embodiments, the epigenetic modifier is a histone deacetylase (HDAC) inhibitor, DNA methyltransferase (DNMT) inhibitor, or combination thereof. When more than one agent is employed to upregulate expression, any combination may be employed. The combination may encompass two or more of the same type of agent or two or more different types of agents. For example, the cells may be exposed to two types of epigenetic modifiers or one type of epigenetic modifier and a mitogen. When more than one epigenetic modifier is employed, the combination may include two HDAC inhibitors or one HDAC and one DNMT inhibitor, for example.

In one embodiment, provided herein is a method of enhancing potency of immune cells that express at least one therapeutic protein, comprising contacting the immune cells with an effective amount of a mitogen, histone deacetylase (HDAC) inhibitor, and/or deoxyribonucleic acid methyl transferase (DNMT) inhibitor for a time sufficient for expression of said therapeutic protein to increase, as compared to said immune cells not contacted with said mitogen, HDAC inhibitor and/or said DNMT inhibitor. in specific embodiments, the HDAC inhibitor a small chain fatty acid, hyroxamic acid, cyclic peptide, benzamide or a combination thereof. In particular embodiments, the HDAC inhibitor is one or more of trichostatin A, sodium phenylbutyrate, Buphenyl, Ammonaps, Depakote, valproic acid, romidepsin (ISTODAX®), Vorinostat, Zolinza, panobinostat, belinostat, entinostat, JNJ-26481585, MGCD-010, and/or a combination thereof. In other specific embodiments, the DNMT inhibitor is a nucleoside analog, quinolone, active site inhibitor, or a combination of any thereof. Specific DNMT inhibitors may be selected from the group consisting of 5-azacitidine, decitabine, zebularine, SGI-110, SGI-1036, RG108, caffeic acid purum, chlorogenic acid, epigallocatechin galiate, procainamide hydrochloride, MG98, and a combination thereof. In specific cases, the DNMT inhibitor is a ribonucleoside analog or deoxyribonucleoside analog. The DNMT inhibitor may be decitabine or zebularine. The DNMT inhibitor may be 5-azacytidine, such as VIDAZA®.

In embodiments, the immune cells are T cells (including CD4+ T cells, CD8+ T cells, or Treg cells), NK cells, dendritic cells, or a mixture of any thereof.

In some cases, contacting of the immune cells and the mitogen, HDAC inhibitor, and/or DNMT inhibitor is performed in vitro and the contacting may occur in cell culture. In some embodiments, the contacting is performed in a pharmaceutical composition comprising the immune cells and the HDAC inhibitor and/or the DNMT inhibitor. In particular aspects, the contacting is performed in vivo, and the immune cells are T cells in an individual.

In particular aspects, immune cells and the mitogen, HDAC inhibitor or the DNMT inhibitor are administered to an individual separately, such as in separate pharmaceutical formulations. In certain cases, the mitogen, HDAC inhibitor and/or DNMT inhibitor, and the immune cells are administered to the individual in the same pharmaceutical formulation. The mitogen, HDAC inhibitor and/or the DNMT inhibitor, and the immune cells, may be administered to the individual at substantially the same time or at different times.

The mitogen, HDAC inhibitor and/or the DNMT inhibitor, and the immune cells, may be administered to an individual according to the same dosing schedule or according to different dosing schedules. In particular aspects, the mitogen, HDAC inhibitor, and/or DNMT inhibitor are provided to the individual before the individual receives immune cells. In some aspects, the immune cells are contacted with the mitogen, HDAC inhibitor, and/or DNMT inhibitor prior to being delivered to the individual. The immune cells may not be contacted with the mitogen, HDAC inhibitor, and/or DNMT inhibitor prior to being delivered to the individual.

In some cases, the immune cells are contacted with at least one HDAC inhibitor and at least one DNMT inhibitor. In particular embodiments, the immune cells are contacted with said HDAC inhibitor in vitro, and subsequently contacted with said DNMT inhibitor in vivo. The immune cells may be contacted with the DNMT inhibitor in vitro, and subsequently contacted with said HDAC inhibitor in vivo. The expression of the therapeutic protein in the immune cells may be controlled by a promoter at least a portion of the sequence of which is methylated, and wherein the methylation results in partial or complete silencing of expression of said therapeutic protein. The expression of the therapeutic protein in the immune cells may be controlled by a promoter repressor region, at least a portion of the sequence of which is methylated, and wherein the methylation results in enhanced expression of said therapeutic protein.

Immune cells may be contacted with two or more HDAC inhibitors, with two or more DNMT inhibitors, or with two or more mitogens. In some cases, the immune cells are contacted with an HDAC inhibitor and a DNMT inhibitor or an HDAC inhibitor and a mitogen, or a DNMT inhibitor and a mitogen.

In certain embodiments, the contacting step occurs multiple times in vivo in the individual. In particular aspects, in a second or subsequent contacting step, the immune cells express a different therapeutic protein than immune cells in a first contacting step. In certain cases, in a second or subsequent contacting step, a mitogen, HDAC inhibitor and/or DNMT inhibitor is administered to the individual. The mitogen, HDAC inhibitor, and/or DNMT inhibitor in the second or subsequent contacting step may be different or the same than the mitogen, HDAC inhibitor, and/or DNMT inhibitor in the first contacting step.

In embodiments wherein more than one epigenetic modifier and/or mitogen are exposed to immune cells expressing one or more therapeutic proteins, the multiple agents may be exposed to the cells in any suitable chronology, dosing schedule, and/or formulation(s). In specific embodiments, the two or more agents are provided to an individual prior, during, and/or after delivery of the immune cells and are provided at the same time, although in some cases they are provided at different times. When multiple agents are delivered to an individual, they may be comprised in the same or different formulations, and they may be delivered by the same or different routes to the individual when they are not in the same formulation. When multiple agents are provided to immune cells and/or an individual, the agents may have the same or different dosing schedule and/or doses.

In specific embodiments, the therapeutic protein expressed by the immune cells is a receptor. In specific cases, the receptor targets an antigen on a cancer cell. The therapeutic protein may be of any kind, such as a chimeric antigen receptor (CAR), cytokine, cytokine receptor, ligand trap, antibody (including a monomeric or multimeric antibody), an engineered αβT cell receptor, or an antigen-specific receptor. In cases where an immune cell expresses more than one therapeutic protein, the therapeutic proteins may be of the same type (both CARs, for example) or may be of different types (CAR and an engineered αβT cell receptor). When the immune cells express more than one therapeutic protein, they may both be upregulated in expression upon exposure to the one or more agents.

The therapeutic protein may be of any kind, but in specific embodiments, it is a chimeric antigen receptor (CAR). The CAR may comprise at least one extracellular antigen-binding domain and at least one intracellular signaling domain. In certain aspects, the therapeutic protein is a cytokine, cytokine receptor, or ligand trap. The therapeutic protein may be a monomeric or multimeric antibody. The therapeutic protein may be a αβT cell receptor or an antigen-specific receptor. In specific embodiment, the immune cells are autologous or allogeneic to a particular individual. The therapeutic protein may be a transgenic protein.

Immune cells may comprise two or more different therapeutic proteins. In some cases, the two different therapeutic proteins are both receptors. In particular embodiments, the two different therapeutic proteins are both CARs. In some cases, one of the two different therapeutic proteins is a CAR and one of the two different therapeutic proteins is an antibody or one of the two different therapeutic proteins is a CAR and one of the two different therapeutic proteins is an αβT cell receptor, or one of the two different therapeutic proteins is a CAR and one of the two different therapeutic proteins is an antigen-specific receptor.

In specific embodiments, there are immune cells that comprise more than one CAR and/or that comprise one or more CARs that target at least two antigens. The target antigens may be cancer antigens of any kind. In specific embodiments the CARs target MUC1 and PSCA, both of which are expressed on approximately 60% of human primary pancreatic cancer cells, as an example. As described herein, there is characterization in an exemplary embodiment of a pancreatic tumor model whether immune escape could be prevented by co-administering CAR-T cells targeting two antigens present on the tumor cells. As expected, when tested individually, selective pressure resulted in the emergence of a tumor subpopulation that lacked or had downregulated the target antigen, rendering the tumor insensitive to subsequent T cell retreatment. Unexpectedly, however, it was determined that the co-administration of CAR-T cells simultaneously targeting both TAAs, though associated with superior anti-tumor effects, was also insufficient to produce tumor elimination.

When the immune cells are modified or engineered to express more than one therapeutic protein, the therapeutic proteins may be delivered to the immune cells in the form of nucleic acids capable of expressing the therapeutic proteins. Such nucleic acids may be expression constructs comprising regulatory sequences that control expression of the therapeutic protein(s). In cases wherein expression construct(s) are delivered to the immune cells such that more than one therapeutic protein is to be expressed by the immune cells, the therapeutic proteins may or may not be encoded from the same expression construct. In specific embodiments of the expression construct, there may be more than one regulatory sequence that regulates expression of the therapeutic protein. In specific embodiments, the regulatory sequences may be a promoter. In particular embodiments, at least a portion of the promoter is methylatable. In specific embodiments, at least a portion of the promoter is methylated. In particular embodiments, methylation of the promoter results in partial or complete silencing of expression of the therapeutic protein. In specific embodiments, the promoter comprises one or more CpG islands.

In certain embodiments, a particular individual is treated with more than one exposure to immune cells comprising at least one therapeutic protein; that is, the individual is administered a dose of the immune cells two or more times during the course of therapy. In second or more exposures to therapeutic-protein comprising immune cells, the individual may be provided immune cells expressing the same therapeutic protein(s). In certain cases, however, the individual may be provided immune cells expressing different therapeutic proteins. In cases wherein an individual is provided two or more exposures to the cells, the individual and/or the cells are also again contacted with one or more agents that upregulate expression of the therapeutic protein. In cases where the second or subsequent rounds have immune cells with different therapeutic proteins compared to the initial round of immune cells, the different therapeutic proteins may or may not target the same antigen. In cases where the second or subsequent immune cells comprise a therapeutic protein that targets a different antigen, the second or subsequent antigen may reside on cancer cells that also expressed the first targeted antigen. For example, pancreatic cancer cells often comprise the tumor associated antigens (TAA) mucin1 (MUC1) and prostate stem cell antigen (PSCA), and the first set of immune cells may target MUC1, whereas the second or a subsequent set of immune cells may target PSCA (or vice versa).

For a particular target (e.g., tumor associated antigen or tumor specific antigen), in certain embodiments, it is assumed that tumor escape will occur, and a second round of treatment with the immune cells expressing a therapeutic protein incorporates contacting the recipient with the epigenetic modifier agent or mitogenic agent, e.g., in an amount that results in increased expression of the therapeutic protein. In other embodiments, upon the second round of treatment with the immune cells expressing a therapeutic protein, the recipient of the cells may be monitored for evidence of tumor escape (e.g., by sampling tissue from the recipient and analyzing for one or more tumor markers (e.g., TAAs or TSAs), and administering the epigenetic modifier agent and/or mitogenic agent upon evidence of tumor escape (e.g., recurrence).

In some embodiments, the immune cells encompass an inducible suicide gene, such as an inducible caspase, e.g., caspase-9, e.g., iCaspase9, Herpes Simplex Virus (HSV) thymidine kinase (TK) gene, cytosine daminase, purine nucleoside phosphorylase, diphtheria toxin, and nitroreductase.

In particular embodiments, an individual is provided an additional therapy in addition to the immune cells/agent of the disclosure. For example, an individual with cancer may receive the immune cells/agent therapy as encompassed herein and additionally receives an additional therapy, e.g., one or more of chemotherapy chemotherapy (e.g., with an agent that is not a mitogenic agent or an epigenetic modifier agent), radiation therapy, hormone therapy, immunotherapy, and surgery. The individual may be administered the additional therapy before, during, or after, or a combination thereof, administration of the immune cells and agent therapy.

In some embodiments, the methods comprise diagnostic steps wherein an individual is diagnosed with cancer, such as using standard means in the art, including biopsy, cancer marker analysis, histology, and so forth, for example. In some embodiments, an individual is suspected of having cancer or has the recurrence of cancer and is provided the therapy described herein. In certain embodiments, an individual is at risk of having cancer or is at risk of having the return of cancer and is provided the therapy described herein.

One embodiment provides a method of treating and/or preventing cancer in an individual, comprising administering to the individual the immune cells and agents that upregulate expression of therapeutic proteins in an amount effective to treat and/or prevent cancer in the individual. The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

The individual referred to herein can be any individual. The individual may be a mammal, including a human, dog, cat, horse, and so forth.

In any of the embodiments herein, the cancer is primary cancer or metastatic cancer. The cancer may be, e.g., a solid tumor or a blood cancer. With respect to the inventive methods, the cancer can be any cancer, including any of acute lymphocytic cancer, acute myeloid leukemia, alveolar rhabdomyosarcoma, bladder cancer, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, Hodgkin lymphoma, hypopharynx cancer, kidney cancer, larynx cancer, leukemia, liquid tumors, liver cancer, lung cancer, lymphoma, malignant mesothelioma, mastocytoma, melanoma, multiple myeloma, nasopharyngeal cancer, non-Hodgkin lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer, and urinary bladder cancer.

DESCRIPTION OF THE DRAWINGS

For a more complete understanding of the present embodiments, reference is made to the following descriptions taken in conjunction with the accompanying drawings.

Figure 1:
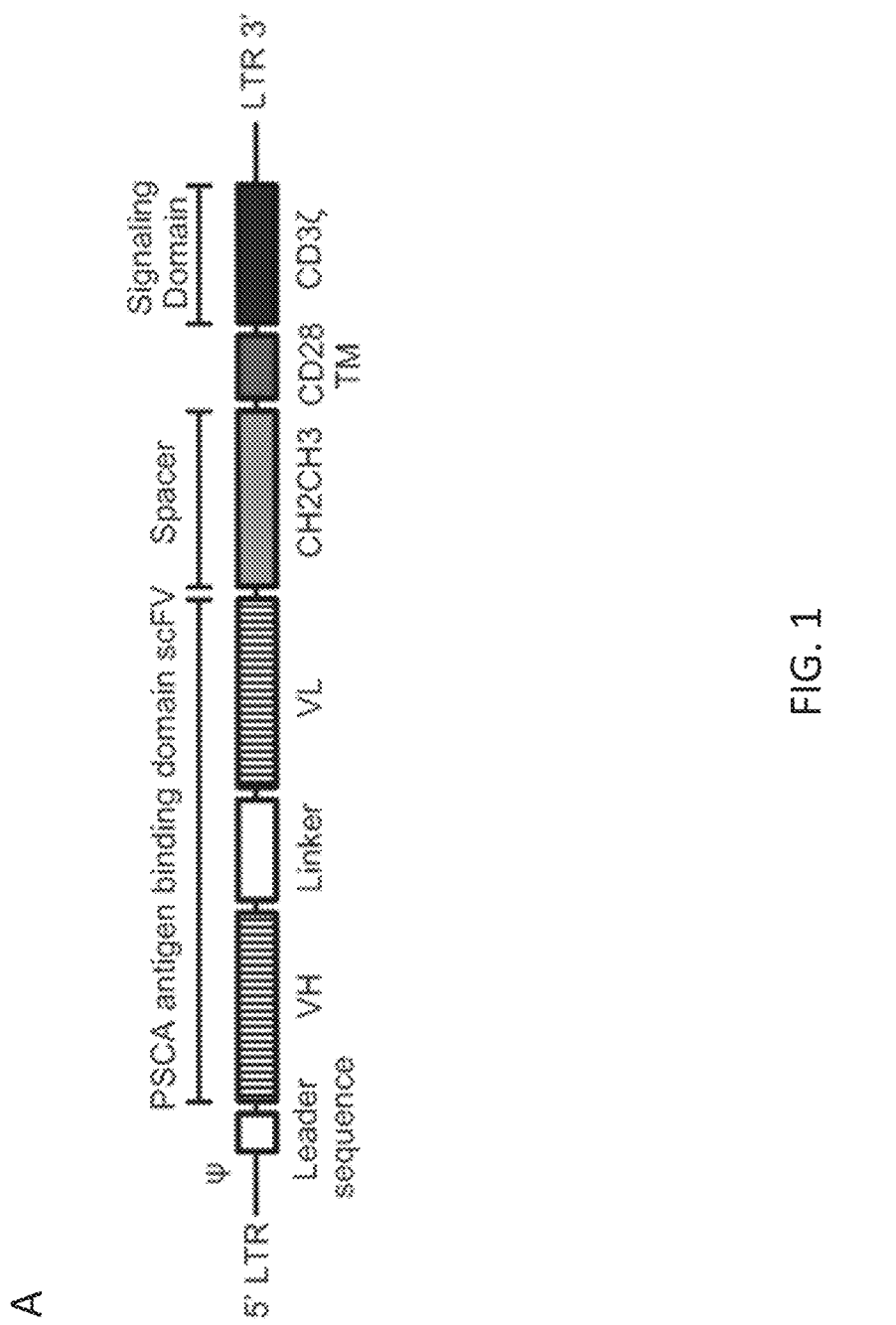
FIG. 1 shows that T cells can be engineered to recognize and kill pancreatic cancer cells expressing PSCA. (a) Retroviral vector map of a first generation humanized, codon-optimized CAR specific for PSCA, (b) left panel, a dot plot from a representative donor showing control (NT) and CAR-PSCA transgenic (CH2CH3 positive) cells; right panel, summary transduction efficiency data for 10 donors, represented as mean±standard deviation (SD) is shown, (c) Phenotype of NT and CAR-PSCA T cells, n=10, (d) 6-hr chromium release assay of CAR-PSCA and NT T cells using PSCA+ (CAPAN1) and PSCA− (293T cells) as targets. Data represents the mean±SD target specific lysis at an E:T of 10:1 (n=5).
Figure 1:
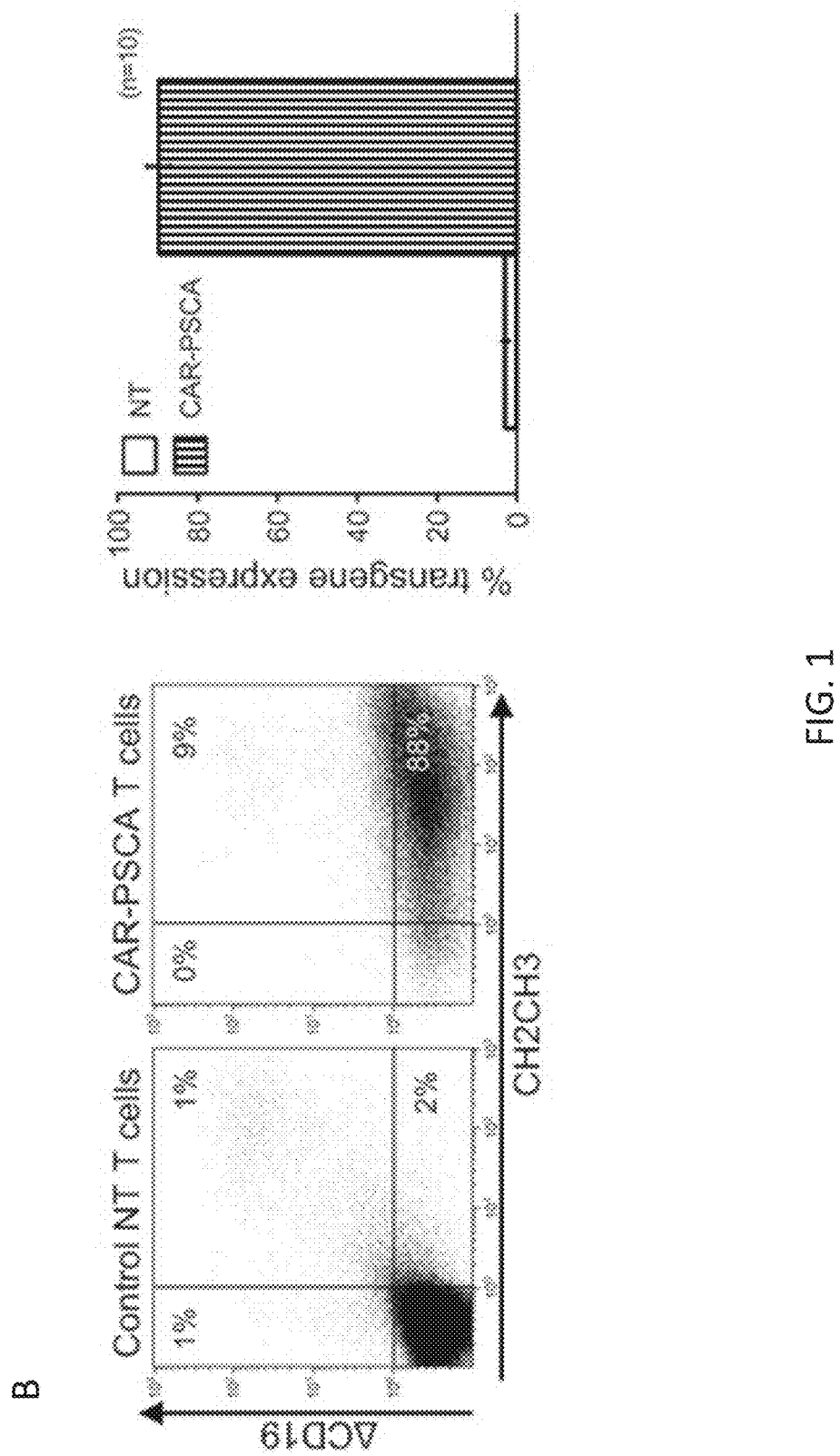
Figure 1:
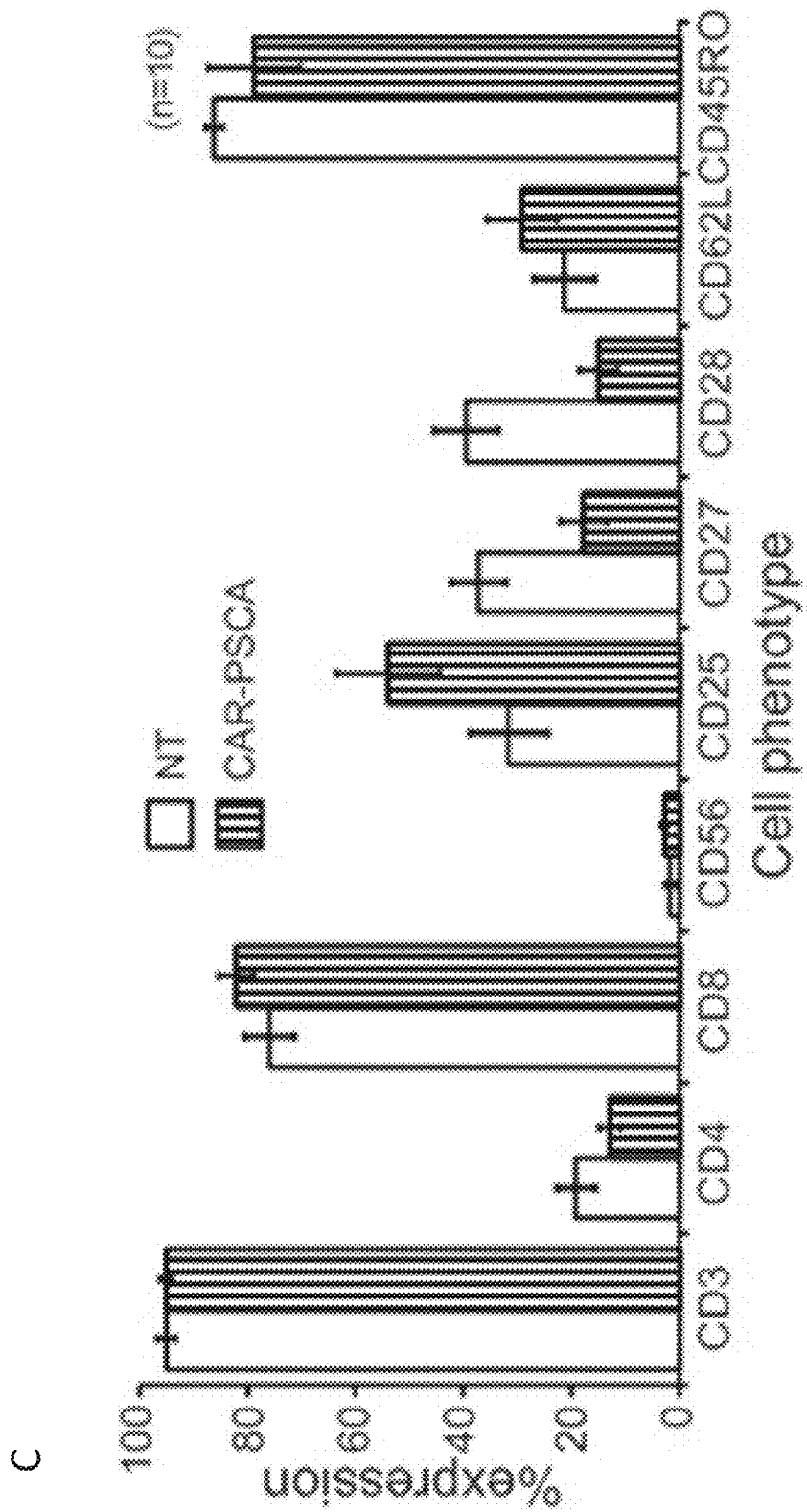
Figure 1:
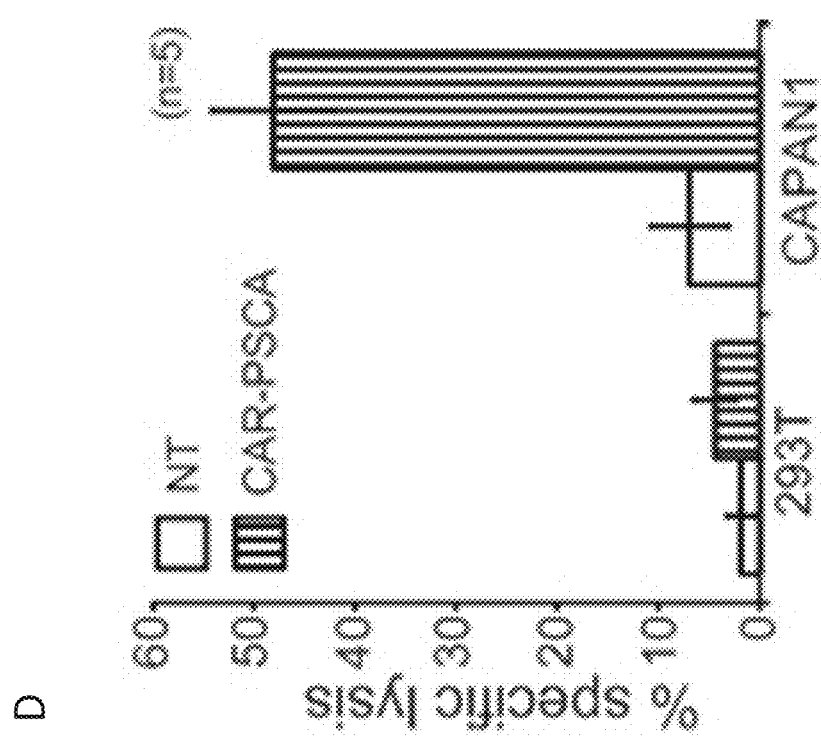

The foregoing has outlined rather broadly the features and technical advantages of the present subject matter in order that the detailed description of the methods provided herein that follows may be better understood. Additional features and advantages of the methods provided herein will be described hereinafter which form the subject of the claims. It should be appreciated by those skilled in the art that the conception and specific embodiments disclosed may be readily utilized as a basis for modifying or designing other structures for carrying out the same purposes. It should also be realized by those skilled in the art that such equivalent constructions do not depart from the spirit and scope of the subject matter as set forth in the appended claims. The novel features which are believed to be characteristic of the methods provided herein, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the methods provided herein.

DETAILED DESCRIPTION

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the subject matter may "consist essentially of" or "consist of" one or more elements or steps of the subject matter, for example. Some embodiments of the subject matter may consist of or consist essentially of one or more elements, method steps, and/or methods of the subject matter. It is contemplated that any method or composition described herein can be implemented with respect to any other method or composition described herein.

As used herein, the term "enhancing the potency of immune cells" is defined as an increase or improvement in the biological properties (natural or recombinant in origin) of a given cell. These biological properties can include, but are not restricted to (i) antigen specificity, (ii) proliferation, (iii) migration, (iv) persistence, and/or (v) killing ability. Additionally, immune cells can be enhanced with recombinant modifications such as (i) resistance to the immunosuppressive tumor microenvironment, (ii) resistance to drugs, and/or (iii) suicide genes.

I. Immunotherapy Methods for Antitumor Activity

In various embodiments, immunotherapy methods for employing immune cells for antitumor activity are provided. Methods of killing tumor cells are contemplated herein employing immune cells that express at least one therapeutic protein. Methods comprise administering to an individual one or more immune cells that have been contacted in vitro or in vivo with an agent that upregulates expression of a therapeutic protein in the immune cell. In certain embodiments, the agent is a HDAC inhibitor, DNA methyl transferase inhibitor, mitogen, or combination thereof. In specific embodiments, one or more target proteins on tumor cells are also increased in expression upon exposure of the tumor cells to immune cells having unregulated expression of the therapeutic protein(s).

In particular embodiments, particular dosing regimens to provide compositions of the invention to an individual in need of cancer treatment are provided. Such regimens include compositions for upregulation of expression of the therapeutic protein in the immune cell in addition to the cells themselves. For example, an agent that facilitates upregulation in expression of the therapeutic protein in an immune cell may be provided to the immune cell prior to delivery of the cell to the individual, and/or it may be provided to the cell subsequent to the delivery of the cell to the individual. The immune cell(s) and the agent may be provided to the individual separately or together, and they may or may not be in the same formulation, and they may or may not be provided at the same time to the individual. In certain embodiments, more than one HDAC inhibitor, DNA methyl transferase inhibitor, and/or mitogen are exposed to the immune cells in vitro and/or in vivo, and the order in which they are exposed to the immune cells may be of any suitable kind so long as expression of at least one therapeutic protein expressed by the cells is increased.

In certain embodiments, an individual is treated for cancer by providing to the individual an effective amount of a combination of immune cells expressing one or more therapeutic proteins and one or more epigenetic modulators and/or mitogenic agents. The treatment may utilize modulation of immune cells (such as T cells) from the individual, e.g., ex vivo modulation such that the immune cells express a therapeutic protein and the cells are subsequently exposed to one or more epigenetic modifiers and/or mitogenic agents prior to and/or subsequent to delivery to the individual.

In some embodiments, immune cells as described herein, once transferred to an individual, have a positive bystander effect on the endogenous immune system by, i) producing proinflammatory cytokines, ii) recruiting additional immune cells such as NK cells and APCs to the tumor site, and iii) inducing epitope spreading. Thus, in specific embodiments adoptive transfer of the immune cells is useful to trigger a cascade of events in vivo that amplifies the anti-tumor activity. In certain embodiments, even in the absence of use of the epigenetic modifier(s) and/or mitogenic agent, immune cells, e.g., dual targeted CAR-T cells, suffice to reactivate a potent endogenous tumor-targeted immune response that will produce tumor elimination.

II. Immune Cells

Immune cells are utilized herein as the means by which a therapeutic protein is delivered to a desired location in an individual in need of therapy. The immune cells are modified such that they express at least one therapeutic protein and, in specific embodiments, the therapeutic protein allows targeting of the immune cells to a target that recognizes the therapeutic protein. In specific embodiments, the therapeutic protein is a receptor or an antibody on the immune cell and the target is an antigen. In specific embodiments, the antigen is a cancer antigen and, if on a solid tumor cell, the antigen may be referred to as a tumor antigen.

In particular embodiments, methods and compositions for immunotherapy are provided, wherein the immunotherapy encompasses modified immune cells. The immune cells are modified to express one or more therapeutic proteins, the expression of which is in need of being maintained at a level sufficient to render the cell effective for immunotherapy. The immune cells may be of any kind, although in specific embodiments they are T cells. The immune cells are exposed, such as directly, with an agent that upregulates expression of the therapeutic protein(s). The immune cells may be contacted with an agent prior to delivery to an individual in need thereof and/or the immune cells may be contacted with an agent subsequent to delivery to an individual in need thereof. The cells may be contacted directly with the agent(s) in vitro or ex vivo, and/or the cells may be contacted in vivo with the agent upon systemic and/or localized delivery of the agent to an individual prior to, during, and/or after delivery of the cells to the individual.

In specific embodiments, the immune cells are T cells (e.g., CD4+ T cells, CD8+ T cells, CD4+CD8+ T cells and/or Treg cells), or are NK cells or dendritic cells. As used herein, the term "immune cell" includes the primary subject cell and its progeny. It is understood that progeny are homogeneous but that progeny may not all be identical due to deliberate or inadvertent mutations. In the context of expressing a heterologous nucleic acid sequence, the immune cell is a cell that is capable of replicating a vector and/or expressing a heterologous gene encoded by a vector. In particular embodiments, an immune cell is engineered to express an exogenous nucleic acid encoding a therapeutic protein by transducing the cell with a viral vector comprising the exogenous nucleic acid. In certain embodiments, the viral vector is a retroviral vector. In one embodiment, the retroviral vector is a lentiviral vector. An immune cell may be engineered to express an exogenous nucleic acid, e.g, a nucleic acid contained in a vector, e.g., an expression vector.

As used herein, "engineered" or "recombinant" cell refers to a cell into which an exogenous nucleic acid sequence, such as, for example, a vector, has been introduced. Therefore, recombinant cells are distinguishable from naturally occurring cells that do not contain a recombinantly introduced nucleic acid.

Some vectors may employ control sequences that allow it to be replicated and/or expressed in both prokaryotic and eukaryotic cells. One of skill in the art would further understand the conditions under which the above described host cells can maintain and permit replication of at least one vector. Also understood and known are techniques and conditions that would allow large-scale production of vectors, as well as production of the nucleic acids encoded by vectors and their cognate polypeptides, proteins, or peptides.

The immune cells can be autologous cells, syngeneic cells, allogenic cells and even in some cases, xenogeneic cells.

In some embodiments, the cells harbor more than one therapeutic protein, and at least in certain aspects the exposure of the cells (or exposure to the individual receiving the cells) to an epigenetic modifier or mitogenic agent results in upregulation of expression of the two or more therapeutic proteins.

In particular embodiments, the immune cells are genetically engineered to express a therapeutic protein, e.g., a CAR, an engineered αβTCR, and/or antigen-specific receptor.

III. Immune Cells Comprising CAR(s)

In particular aspects, the immune cells are T cells that express a chimeric antigen receptor (CAR). The use of CAR-modified T cells as a therapy for both hematologic malignancies and solid tumors is becoming more widespread. However, the infusion of a T cell product targeting a single tumor associated antigen (TAA) or tumor-specific antigen (TAA) may lead to target antigen modulation under this selective pressure, or may select for tumor cell expressing low levels of the TAA or TSA, with subsequent tumor immune escape. Tumor escape by the same mechanism may occur even when two TAAs or TSAs are targeted. Surprisingly, it has been found that the magnitude of tumor destruction depended not only on the presence of the target antigen but also the intensity of expression. Expression of such TAAs or TSAs may be increased by administering epigenetic modulators that upregulate target expression and enhance CAR-T cell potency, in particular embodiments.

A chimeric antigen receptor (CAR) is an artificially constructed hybrid protein or polypeptide typically containing an extracellular antigen binding domain, a transmembrane domain, and an intracellular signaling domain. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

The phrases "have antigen specificity" and "elicit antigen-specific response" as used herein means that the CAR can specifically bind to and immunologically recognize an antigen, such that binding of the CAR to the antigen elicits an immune response.

The extracellular antigen binding domain may be any protein or portion thereof that binds to a target protein, e.g., a receptor or ligand-binding portion thereof; a ligand of a receptor (e.g., a cytokine); or an antibody or antigen-binding portion of an antibody, e.g., an Fc domain of a single-chain antibody (scFv).

In particular embodiments, a CAR comprises a transmembrane domain selected from the group consisting of: a CD4 transmembrane domain, a CD8 transmembrane domain, and a CD28 transmembrane domain.

The intracellular signaling domain, in certain embodiments, comprises a primary signaling domain, e.g., a T cell receptor zeta chain or primary signaling domain therefrom. In particular embodiments, the intracellular signaling domain further comprises one or more co-stimulatory domains. Illustrative examples of co-stimulatory domains suitable for use in the CARs contemplated herein include, but are not limited to: e.g. CD27, CD28, CD137 (4-1BB), OX-40, or a combination of two, three, or all of the foregoing.

In specific embodiments, the CAR comprises an antibody for the tumor antigen, part or all of a cytoplasmic signaling domain, and/or part or all of one or more co-stimulatory molecules, for example endodomains of co-stimulatory molecules. In specific embodiments, the antibody is a single-chain variable fragment (scFv). In certain aspects the antibody is directed at target antigens on the cell surface of cancer cells, for example. In certain embodiments, a cytoplasmic signaling domain, such as those derived from the T cell receptor zeta-chain, is employed as at least part of the chimeric receptor in order to produce stimulatory signals for T lymphocyte proliferation and effector function following engagement of the chimeric receptor with the target antigen. Illustrative examples include, but are not limited to, endodomains from co-stimulatory molecules such as CD27, CD28, 4-1BB, ICOS (CD278) and OX40, or combinations of two, three, four, or all of the foregoing. In particular embodiments, co-stimulatory molecules are employed to enhance the activation, proliferation, and cytotoxicity of T cells produced by the CAR after antigen engagement. In specific embodiments, the co-stimulatory molecules are CD28, OX40, and 4-1BB.

In one embodiment, the CAR comprises an extracellular hinge domain, transmembrane domain, and optionally, an intracellular hinge domain comprising CD8 sequences and an intracellular T cell receptor signaling domain comprising CD28, 4-1BB, and CD3ζ. CD28 is a T cell marker important in T cell co-stimulation. CD8 is also a T cell marker. 4-1BB transmits a potent costimulatory signal to T cells, promoting differentiation and enhancing long-term survival of T lymphocytes. CD3 ζ associates with TCRs to produce a signal and contains immunoreceptor tyrosine-based activation motifs (ITAMs). In one embodiment, a CAR comprises an extracellular hinge domain, transmembrane domain, and optional intracellular hinge domain.

The CAR may be first generation, second generation, or third generation (CAR in which signaling is provided by CD3ζ together with co-stimulation provided by CD28 and a tumor necrosis factor receptor (TNFr), such as 4-1BB or OX40), for example. The CAR may be specific for PSCA, HER2, CD19, CD20, CD22, Kappa or light chain, Lambda, CD30, CD33, CD123, CD38, ROR1, ErbB2, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α2, IL-11 receptor α, MUC1, MUC16, CA9, CE7, CEA, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, TEM8, sp17, viral-associated antigens expressed by the tumor, or other tumor-associated antigens that are identified through genomic analysis and or differential expression studies of tumors.

In particular embodiments, the CAR is encoded by an expression vector. The vector may be bicistronic, in particular embodiments. In some embodiments, more than one CAR is expressed by the immune cell. In particular embodiments where more than one CAR is to be expressed by the immune cell, the two or more CAR expression constructs may or may not be on the same vector. When present on the same vector, the first CAR coding sequence may be configured 5' or 3' to the second CAR coding sequence. The expression of the first CAR and second or subsequent CAR receptor may be under the direction of the same or different regulatory sequences.

In particular cases, the immune cell comprises the therapeutic protein as a membrane-bound protein. In certain embodiments, the protein is secretable from the immune cell. In particular embodiments, the therapeutic protein is a receptor for a cancer antigen; the cancer antigen (which may be on a solid tumor or not) may be present on the surface of a cancer cell. In specific embodiments, the receptor is a chimeric antigen receptor (CAR). In particular cases, the immune cell is a T cell comprising one, two, three, or more CARs.

In some embodiments wherein the immune cell comprises at least one CAR, the CAR may be directed to any type of cancer antigen. In particular embodiments, the immune cell comprises one CAR directed to one cancer antigen, and another CAR in the same cell directed to another cancer antigen.

In certain embodiments, an individual is provided a therapeutically effective amount of a plurality of immune cells expressing one or more therapeutic proteins. In some embodiments, the individual is subsequently provided a therapeutically effective amount of a plurality of immune cells expressing one or more other therapeutic proteins different from that (or those) initially provided to the individual.

In some situations one may wish to be able to kill the modified immune cells e.g. In particular embodiments, the expression of certain gene products kills the immune cells under controlled conditions, such as inducible suicide genes. Illustrative examples of inducible suicide genes include, but are not limited to: caspase-9 Herpes Simplex Virus (HSV) thymidine kinase (TK) gene, cytosine daminase, purine nucleoside phosphorylase, and nitroreductase.

IV. Agents that Upregulate Expression of a Therapeutic Protein

In various embodiments, an agent that upregulates expression of the therapeutic protein in an immune cell is provided. In certain embodiments, the upregulation is detectable and greater than that expression in the cell in the absence of exposure to the agent. In specific embodiments, the agent(s) upregulates expression of the therapeutic protein at least two-fold, three-fold, four-fold, five-fold, ten-fold, twenty-fold, twenty five-fold, thirty-fold, thirty five-fold, forty-fold, forty five-fold, fifty-fold, one hundred-fold, two hundred-fold, five hundred-fold, one thousand-fold, or more.

In one embodiment, the agent that upregulates expression may be of any kind. In specific embodiments the agent is one or both of an epigenetic modifier, including, but not limited to, an HDAC inhibitor and/or a DNMT inhibitor, and a mitogen.

A. Epigenetic Modifiers

In some embodiments, one or more epigenetic modifiers are utilized in methods and compositions to upregulate expression of one or more therapeutic proteins in an immune cell. The epigenetic modifiers may be of any kind so long as they are capable of upregulating expression of at least one therapeutic protein in an immune cell. One or more types of epigenetic modifiers may be used in the same method or composition. When more than one epigenetic modifier is employed, they may be delivered to cells or to an individual at the same time, at different times, in the same formulation, or in different formulations. In some cases, the epigenetic modifier is a histone deacetylase (HDAC) inhibitor. In some cases, the epigenetic modifier is DNA methyltransferase (DNMT) inhibitor. In certain cases, a combination of HDAC inhibitor and DNMT inhibitor is employed. The epigenetic modifier may be an EZH2 antagonist, such as DZnep or 3-deazaneplanocin A, for example.

In some embodiments, the epigenetic modifier(s) comprises one or more histone deacetylase (HDAC) inhibitors. The HDAC inhibitors include, but are not limited to small chain fatty acids, hyroxamic acids, cyclic peptides, or benzamides. Further illustrative examples of HDAC inhibitors include, but are not limited to, trichostatin A, sodium phenylbutyrate, Buphenyl, Ammonaps, Valproic acid, Depakote, romidepsin (ISTODAX®), Vorinostat, Zolinza, panobinostat, belinostat, entinostat, JNJ-26481585 (Johnson & Johnson; Langhorne, Pa.), and/or MGCD-0103 (MethylGene; Montreal, Canada).

In some embodiments, the epigenetic modifier(s) comprises one or more DNMT inhibitors. The DNMT inhibitors include, but are not limited to nucleoside analogs, quinolone, or active site inhibitors. Further illustrative examples of DNMT inhibitors include but are not limited to 5-azacitidine (such as VIDAZA®), decitabine (e.g., DACOGEN®), zebularine, SGI-110 or SGI-1036 (SuperGen; Dublin, Calif.), RG108, caffeic acid purum, chlorogenic acid, epigallocatechin galiate, procainamide hydrochloride, a procainamide derivative, 5-azadeoxycytidine, 5'-aza-2'-deoxycytidine or MG98.

B. Mitogens

In some embodiments, one or more mitogens are used in methods or compositions. The mitogen(s) may be provided to an individual in need thereof or to immune cells that are to be delivered to an individual in need thereof. The mitogen may be used as the only type of agent, or the mitogen may be used in combination with another agent, including a HDAC inhibitor and/or DNMT inhibitor, for example. Illustrative examples of mitogens include but are not limited to concanavalin A, phytohaemagglutinin, lipopolysaccharide, and pokeweed mitogen.

V. Delivery of the Agent(s) to Cells and/or Individuals

In particular embodiments, in vivo or in vitro or ex vivo methods are provided and in some embodiments part of the method may be in vitro or ex vivo, followed by an in vivo step, for example.

In particular in vitro embodiments, a plurality of immune cells may be obtained. The cells may be obtained from an individual and manipulated and ultimately delivered back into the same individual. The cells may be obtained from an individual, manipulated, and ultimately delivered into another individual. In some cases, the immune cells are obtained from a repository or commercially, for example.

Prior to exposure of the cells to an agent, the immune cells may be manipulated in one or more of a variety of ways. In specific embodiments, a nucleic acid is introduced into the cells, such as by standard means. The nucleic acid may be at least one vector with at least one expression construct that encodes at least one therapeutic protein, for example. In particular embodiments, the therapeutic protein is a receptor, cytokine, ligand trap, or antibody (including monomeric or multimeric). In specific embodiments, the therapeutic protein is a chimeric antigen receptor (CAR) or cytokine receptor.

In some embodiments, the cells are manipulated such that they encompass more than one therapeutic protein, and there may be mechanisms to monitor retention of the two or more therapeutic proteins in the cell(s), such as labels and/or selectable markers.

In particular embodiments, the cells of the in vitro or ex vivo method are expanded, such as by routine methods in the art Exposure of the cells to an epigenetic modifier agent or mitogenic agent may occur by any suitable regimen so long as the cells receive a sufficient amount of the agent and for a sufficient time to upregulate expression of the therapeutic protein. In some embodiments, the agent is delivered to the immune cells more than once prior to delivery of the cells to the individual. In certain embodiments, more than one agent is provided to the immune cells at the same or different times prior to the delivery of the cells to the individual, and the agent may be of the same or different types, such as one HDAC inhibitor and one DNMT inhibitor, for example. When an individual is pre-treated with an epigenetic modifier agent or mitogenic agent prior to the delivery of the cells to the individual, that agent or agents may or may not be the same agent or agents provided to the cells prior to delivery to the individual. In some cases, the cells are not exposed to an epigenetic modifier agent or mitogenic agent prior to the delivery of the cells to the individual.

In particular embodiments, an individual in need of treatment with the immune cells/agent are exposed to the agent prior to receipt of the cells, although in specific embodiments, the individual may be exposed to the agent following receipt of the cells in addition to or as an alternative to exposure to the agent prior to receipt of the cells. In particular embodiment, the individual is provided with pre-treatment of the agent in multiple doses. The agent may be delivered to the individual by any suitable means, although in specific embodiments the delivery is oral, subcutaneous, intravenous, intramuscular, intraperitoneal, buccal, and so forth. When more than one agent is delivered to the individual, the agents may be delivered by separate delivery means, although in particular embodiments, the agents are delivered by the same route and may or may not be in the same formulation.

In some embodiments, the individual receives the immune cells multiple times, and the separate deliveries may be separated by a space of time of minutes, days, weeks, months, or years. In these cases, the separate courses of delivery of the cells may encompass immune cells having the same or different therapeutic proteins. The individual may in subsequent rounds be exposed to treatment of the same or different agent than the agent that the individual was treated with in the initial round. Any round of exposure of the cells to the individual may encompass pre-treatment and/or post-treatment with the agent.

VI. Pharmaceutical Compositions

With respect to pharmaceutical compositions comprising the agents and/or the cells, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular material, as well as by the particular method used to administer the inventive material. Accordingly, there are a variety of suitable formulations of the pharmaceutical composition of the invention. Preservatives may be used. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

Methods for preparing administrable (e.g., parenterally administrable) compositions are known or apparent to those skilled in the art and are described in more detail in the *Physicians Desk Reference,* 62nd edition. Oradell, N.J.: Medical Economics Co., 2008; Goodman & Gilman's *The Pharmacological Basis of Therapeutics*, Eleventh Edition. McGraw-Hill, 2005; *Remington: The Science and Practice of Pharmacy,* 21$^{st}$ Edition. Baltimore, Md.: Lippincott Williams & Wilkins, 2005; and *The Merck Index*, Fourteenth Edition. Whitehouse Station, N.J.: Merck Research Laboratories, 2006; each of which is hereby incorporated by reference in relevant parts.

The following formulations for oral, aerosol, parenteral (e.g., subcutaneous, intravenous, intraarterial, intramuscular, intradermal, interperitoneal, and intrathecal), and topical administration are merely exemplary and are in no way limiting. More than one route can be used to administer the inventive CAR materials, and in certain instances, a particular route can provide a more immediate and more effective response than another route.

Formulations suitable for oral administration include liquid solutions optionally comprising diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or softshelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise flavoring compounds, usually sucrose and acacia or tragacanth, as well as pastilles in an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive. CAR material can be administered in a physiologically acceptable diluent in a pharmaceutical carrier, such as a sterile liquid or mixture of liquids, including a pharmaceutically acceptable cell culture medium, water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain, for example, from about 0.5% to about 25% by weight of the active agents or cells in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with an embodiment of the invention. The requirements for effective pharmaceutical carriers for injectable compositions are well-known to those of ordinary skill in the art (see, e.g., Pharmaceutics and Pharmacy Practice, J.B. Lippincott Company, Philadelphia, Pa., Banker and Chalmers, eds., pages 238-250 (1982), and ASHP Handbook on Injectable Drugs, Toissel, 4th ed., pages 622-630 (1986)).

Topical formulations, including those that are useful for transdermal drug release, are well known to those of skill in the art and are suitable in the context of embodiments of the invention for application to skin. The compositions contemplated herein can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

An "effective amount" or "an amount effective to treat" refers to a dose that is adequate to prevent or treat cancer in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the agents and/or cells contemplated herein, in each or various rounds of administration. By way of example and not intending to limit the invention, the dose of the compositions can be about 0.001 to about 1000 mg/kg body weight of the subject being treated/day, from about 0.01 to about 10 mg/kg body weight/day, about 0.01 mg to about 1 mg/kg body weight/day.

It can generally be stated that a pharmaceutical composition comprising the T cells described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present invention, particularly since all the infused cells will be redirected to a particular target antigen, lower numbers of cells, in the range of $10^6$/kilogram ($10^6$-$10^{11}$ per patient) may be administered. CAR expressing cell compositions may be administered multiple times at dosages within these ranges.

For purposes of the invention, the amount or dose of compositions contemplated herein administered should be sufficient to effect a therapeutic or prophylactic response in the subject or animal over a reasonable time frame. For example, the dose of a composition should be sufficient to bind to antigen, or detect, treat or prevent disease in a period of from about 2 hours or longer, e.g., about 12 to about 24 or more hours, from the time of administration. In certain embodiments, the time period could be even longer. The dose will be determined by the efficacy of the particular composition and the condition of the animal (e.g., human), as well as the body weight of the animal (e.g., human) to be treated.

Delivery systems useful in the context of embodiments contemplated herein may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

VII. Combination Treatments

In certain embodiments, one or more medical treatments may be provided to an individual in addition to the immune cells and/or epigenetic modifying or mitogenic agent that themselves comprises a therapeutic agent. The one or more other medical treatments may be suitable for any kind of medical condition, but in particular embodiments the medical condition is cancer.

In specific embodiments, the combination therapy comprises one or more anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the nanoparticle and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the nanoparticles and the other includes the second agent(s).

In the context of the present invention, it is contemplated that the present therapy could be used similarly in conjunction with chemotherapeutic, radiotherapeutic, or immunotherapeutic intervention, for example. Alternatively, the present therapy may precede or follow the other treatment by intervals ranging from minutes to weeks. In some embodiments where the other therapy and present therapy are applied separately to the cell or individual, one would generally ensure that a significant period of time did not expire between the time of each delivery, such that the agent and present therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, such as wherein nanoparticle therapy is "A" and the secondary agent, such as radio- or chemotherapy, is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the therapeutic nanoparticles of the present invention to a patient will follow general protocols for the administration of chemotherapeutics, in some cases. It is expected that the treatment cycles would be repeated as necessary. It also is contemplated that various standard therapies, as well as surgical intervention, may be applied in combination with the present hyperproliferative therapy.

A. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristine, vinblastin and methotrexate, or any analog or derivative variant of the foregoing.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

An immunotherapy other than that of the present disclosure may be employed in addition in particular embodiments. Immunotherapeutics, generally, rely on the use of immune effector cells and molecules to target and destroy cancer cells, and immunotherapies other than the present invention may be employed in addition to the present embodiments. The alternative therapy may or may not be comprised on the immune cells contemplated herein.

The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as a two-pronged approach for the combined therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Gene Therapy

In yet another embodiment, the secondary treatment may be a gene therapy in which a therapeutic polynucleotide is administered before, after, or at the same time as the present therapy. The therapeutic polynucleotide may encode all or part of a therapeutic polypeptide or the polynucleotide may be therapeutic itself (such as miRNA, siRNA, shRNA). Delivery of a vector encoding either a full length or truncated therapeutic polypeptide or a therapeutic polynucleotide in conjunction with therapy of the present disclosure will have a combined anti-hyperproliferative effect on target tissues.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

VIII. Kits

Any of the compositions described herein may be comprised in a kit. In a non-limiting example, there may be an epigenetic modifier and/or mitogenic agent and/or immune cells and/or an apparatus for extracting immune's cells that are autologous or allogeneic compared to an individual. One or more therapeutic or other agents may be comprised in a kit, such as another type of therapy, including a drug(s), such as a cancer drug. In some embodiments, reagents for expansion of immune cells may be included. Other compositions may include standard buffers, salts, and the like. The kit will comprise its components in suitable container means. Such components may be suitably aliquoted. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a container. The kits of the present invention also will typically include a means for containing the component containers in close confinement for commercial sale. Such containers may include injection or blow-molded plastic containers into which the desired vials are retained.

When the components of the kit are provided in one and/or more liquid solutions, the liquid solution may be an aqueous solution, with a sterile aqueous solution being particularly preferred. The compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

Irrespective of the number and/or type of containers, the kits of the invention may also comprise, and/or be packaged with, an instrument for assisting with the injection/administration and/or placement of the ultimate composition within the body of an animal. Such an instrument may be a syringe, pipette, forceps, and/or any such medically approved delivery vehicle.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods and Materials

Exemplary materials and methods are provided herein.
Donor and Cell Lines

The pancreatic cancer cell line, CAPAN1, which naturally express PSCA and MUC1, and human embryonic kidney cell line, 293T, were obtained from the American Type Culture Collection (ATCC; Rockville, Md.). Cells were maintained in complete IMDM media (IMDM; Gibco by Life Technologies Corporation, Grand Island, N.Y.), 10% FBS (Hyclone Laboratories, Inc., Logan, Utah) and 2 mM L-glutaMAX (Gibco by Life Technologies Corporation, Grand Island, N.Y.) and a humidified atmosphere containing 5% carbon dioxide ($CO_2$) at 37° C. Peripheral blood mononuclear cells (PBMCs) from healthy volunteers were obtained with informed consent on protocols approved by the Baylor College of Medicine Institutional Review Board.

OKT3/CD28 Blast Generation

PBMCs obtained from healthy donors were activated with OKT3 (1 mg/ml) (Ortho Biotech, Inc., Bridgewater, N.J.) and CD28 antibodies (1 mg/ml) (Becton Dickinson & Co., Mountain View, Calif.) and plated in a non tissue culture-treated 24-well plate at $1 \times 10^6$ PBMCs/2 ml in complete media (RPMI 1640; Hyclone Laboratories, Inc., Logan, Utah) containing 45% Clicks medium (Irvine Scientific, Inc., Santa Ana, Calif.), 10% FBS (Hyclone Laboratories, Inc., Logan, Utah) and 2 mM L-glutaMAX (Gibco by Life Technologies Corporation, Grand Island, N.Y.) and subsequently split and fed with fresh media plus IL2 (50 U/ml).

Generation of Retroviral Constructs and Retroviral Transduction

A codon-optimized single chain variable fragment (scFV) of MUC1 and a humanized, codon-optimized scFV of PSCA were synthesized (DNA 2.0, Menlo Park, Calif.) based on published sequences. The scFV fragments were cloned in-frame with the human IgG1-CH2CH3 domain and with the ζ-chain of the TCR/CD3 complex in the SFG retroviral backbone, to make first generation CAR-PSCA and CAR-MUC1 retroviral constructs. In order to distinguish CAR-modified T cells ΔCD19 (T cells modified to express a beta cell marker, for ease of identification) was incorporated into the CAR-MUC1 retroviral vector using an IRES element. To generate $2^{nd}$ and $3^{rd}$ generation CAR-PSCA constructs the CD28 endodomain or CD28 and 41BB costimulatory endodomains were added to the first generation CAR between the IgG1-CH2CH3 domain and the TCR/CD3ζ endodomain. Also synthesized (DNA 2.0, Menlo Park, Calif.) were the TAAs MUC1 and PSCA, based on published sequences. The fluorescent markers mOrange and green fluorescence protein (GFP) were incorporated into the MUC1 antigen and the PSCA antigen vectors, respectively, again using an IRES element. Retroviral supernatant was produced as previously described, filtered (using a 0.45-mm filter) and stored at –80° C.

T Cell Transduction

For T cell transduction, CAR-MUC1 or CAR-PSCA retroviral supernatant was plated in a non-tissue culture-treated 24-well plate (1 ml/well), which was pre-coated with a recombinant fibronectin fragment (FN CH-296; Retronectin; Takara Shuzo Co. Ltd, Otsu, Japan). OKT3/CD28-activated T cells ($0.2 \times 10^6$/ml in complete media with IL2 100 U/ml) were added to the plates (1 ml/well), and then transferred to a 37° C., 5% $CO_2$ incubator. CAR-T cell expansion was performed in a G-Rex 100M (Wilson Wolf Manufacturing; New Brighton, Minn.) with 1 L of complete media supplemented with IL2 (50 U/ml).

293T Transduction

For transduction, MUC1-mOrange or PSCA-GFP viral supernatant was plated in a retronectin pre-coated 24-well plate (1 ml/well). $0.2 \times 10^5$/ml 293T cells were added to the supernatant (1 ml/well), then the cells were spun at 1000 g for 30 min at room temperature (RT), and transferred to a 37° C., 5% $CO_2$ incubator. Expression of MUC1-mOrange or PSCA-GFP was measured 72 hrs post-transduction by flow cytometry and using a fluorescence microscope to detect the fluorescent markers mOrange and GFP. Cells were maintained or expanded in complete IMDM media every 3-4 days.

Cell Sorting 293T cells were sorted, based on mOrange and GFP expression, using a MoFlo flow cytometer (Cytomation, Fort Collins, Colo.). Sorted cells were cultured in complete IMDM media supplemented with penicillin (100 U/ml), streptomycin (100 µg/ml) and gentamicin (25 µg/ml) (Gibco by Life Technologies Corporation, Grand Island, N.Y.) for one week in a 6-well plate, then further expanded in a T175 flask using complete IMDM media, which was replenished every 3-4 days.

Immunohistochemistry (IHC)

CAPAN1 cells were stained as described previously with either mouse anti-human MUC1 antibody or rabbit anti-human PSCA antibody (AbCam Inc., Cambridge, Mass.) diluted 1:200 and 1:80, respectively, in PBS/1% bovine serum albumin (BSA) for 1 hr at RT and co-stained with anti-mouse horseradish peroxidase (HRP) or anti-rabbit HRP (AbCam Inc., Cambridge, Mass.).

Cytotoxicity

Chromium Release Assay

The cytotoxicity specificity of effector T cell populations was measured in a standard 6 hr $^{51}$Cr release assay, using E:T ratios ranging from 40:1 to 5:1, and using CAPAN1 and 293T cells as targets.

Co-Culture Experiment

CAPAN1, 293T, 293T-MUC1-mOrange or 293T-PSCA-GFP, were used as targets. Briefly, GFP/CAPAN1 cells were mixed with either OKT3/CD28 blasts or CAR-modified T cells at a 1:5 ratio in the presence of IL2 (50 U/ml) in complete media. For our engineered tumor model, 293T-MUC1-mOrange and 293T-PSCA-GFP (or control 293T cells alone) were mixed at 1:1 ratio then OKT3/CD28 blasts or CAR-modified T cells were added to the mixture; 10:1 (T cells:tumor cell), in the presence of IL2 (50 U/ml) in complete media. After 72 hours all residual cells were collected, counted, stained and then analyzed by flow cytometry (Gallios; Beckman Coulter Inc., Brea, Calif.).

Flow Cytometry

Immunophenotyping

T cells were analyzed 3-4 weeks after the generation of the culture by surface-stained with monoclonal antibodies to: CD3, CD4, CD8, CD19, CD56, CD27, CD28, CD45RO, and CD62L (Becton Dickinson BD, Franklin Lakes, N.J.). Cells were washed once with PBS supplemented with 2% FBS, pelleted, and antibodies added in saturating amounts (10 ul). To detect CAR-transduced cells, T cells were stained with a monoclonal antibody Fc-specific cyanine-Cy5-conjugated antibody (Jackson Immuno Research Laboratories, Inc., West Grove, Pa.), which recognizes the IgG1-CH2CH3 component of the receptor. Cells were analyzed using a Gallios Flow cytometer and the data analyzed using Kaluza software (Beckman Coulter Inc., Brea, Calif.).

MUC1 Antigen Staining

One million CAPAN1 cells were fixed with 80% methanol and washed with 0.1% tween-PBS. 1 ug of anti-MUC1 antibody (Abcam Inc, Cambridge, Mass.) was added and incubated at RT for 30 mins. Then cultures were washed and incubated with 0.4 ug of a goat anti-mouse IgG APC antibody (BD Pharmingen, San Jose, Calif.) for 20 mins at 4° C. in the dark. Cells were then washed twice and analyzed.

In Vivo Study

One million CAPAN1 cells, which were engineered to express eGFP-Firefly luciferase (eGFP-FFLuc), were inoculated intraperitoneally (IP) into SCID mice. Bioluminescence images were recorded once a week using Lumina IVIS imaging system (Caliper Life Sciences Inc., Hopkinton, Mass.), and analyzed by Living Image software. After engraftment, defined as an increase in tumor signal in at least two consecutive bioluminescence measurements, mice were treated IP with CAR-modified T cells (30×10$^6$ cells/animal).

All treated groups received IL-2 (4,000 U/animal) IP three times per week and bioluminescence imaging was done once a week.

Decitabine Treatment

CAPAN1 cells were culture in a T175 flask using complete IMDM media contained 1 μM 5-Aza-2'-deoxycytidine—decitabine—(Sigma-aldrich Inc., Saint Louis, Mo.) for 4 days, with fresh media+decitabine replenished daily. Subsequently, decitabine-treated CAPAN1 cells were rested for 2 days in complete IMDM, and then co-cultured with CAR-MUC1 T cells.

Example 2

T Cells Engineered to Express a Car Targeting PSCA can Kill Antigen-Expressing Targets To target tumors expressing the TAA PSCA, a retroviral vector encoding a humanized, codon-optimized CAR-directed against PSCA was generated. FIG. 1a shows the retroviral vector map and FIG. 1b (left panel) shows CAR expression on T cells from a representative donor, and in summary for all 10 donors studied (FIG. 1b, right panel). A mean of 89.9% (±9% SD) T cells expressed CAR-PSCA, and phenotype was unaffected by CAR transduction (FIG. 1c) so that both non-transduced (NT) and CAR-PSCA transgenic T cells were predominantly CD3+(95.2±5.7% and 95.2±3.5%), with a mixture of CD4+(19.2±12.0% and 12.8±6.3%) and CD8+(76.1±15.5% and 82.2±10.5%) populations. CD56+ CD3− NK cells comprised 1.7±3.0% and 2.7±2.2% of the NT and CAR-PSCA transduced populations. The same proportion of CD3+ T cells in both NT and transduced populations expressed the central memory markers CD62L, CD27 and CD45RO. FIG. 1d demonstrates that CAR-modified T cells were able to kill PSCA+ pancreatic cancer cells CAPAN1 (48±6% specific lysis at 10:1 E:T ratio), but not PSCA negative 293T targets, and NT T cells produced only background levels of lysis (7±4% and 4±1% specific lysis of CAPAN1 and 293T cells, respectively).

Example 3

Figure 2:
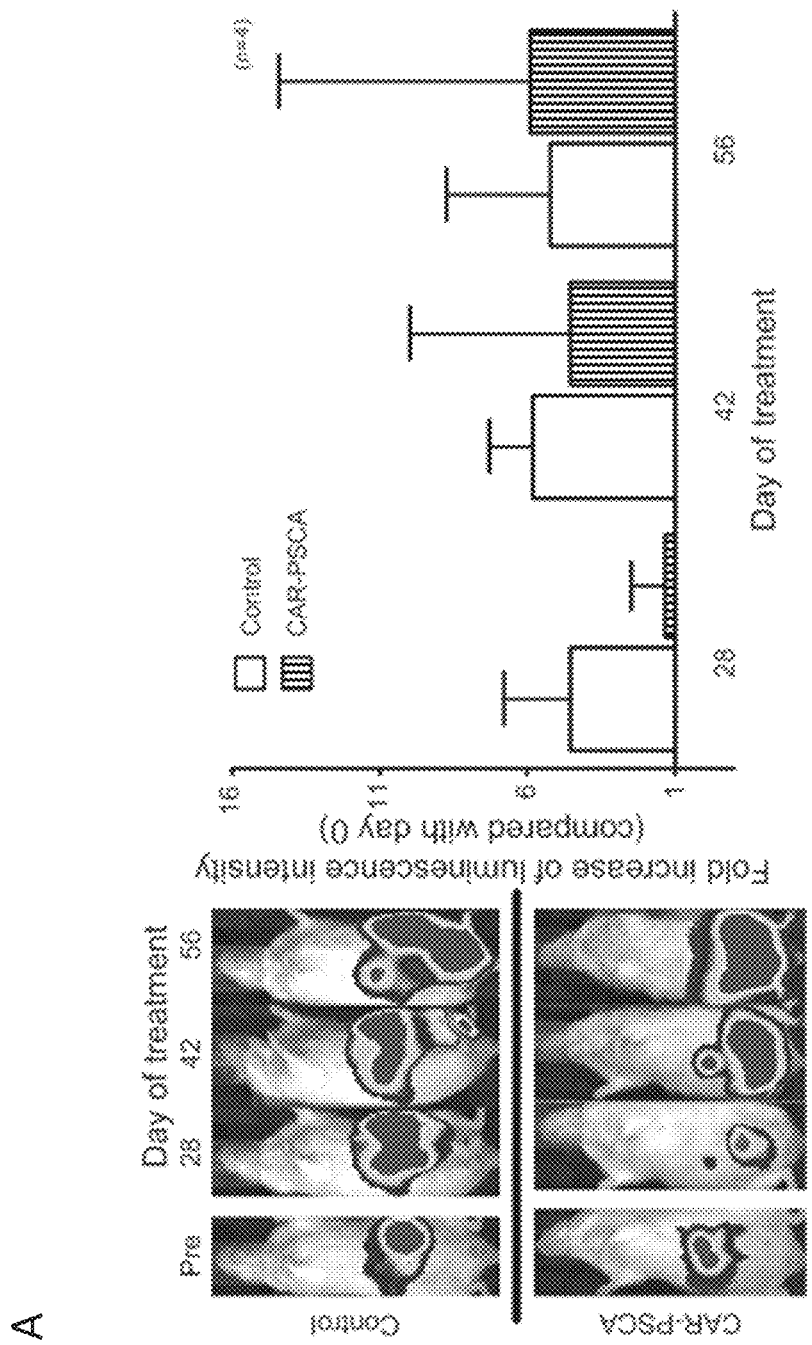
FIG. 2 demonstrates that targeting of a heterogeneous tumor with monospecific CAR-T cells leads to tumor immune escape. To assess whether CAR-PSCA could control CAPAN1 tumor growth in vivo SCID mice were engrafted with tumor cells. (a, left panel) shows bioluminescence images of a representative untreated mouse (top) or an animal treated with CAR-PSCA T cells at pre or 28, 42 or 56 days post treatment, while the right panel shows summary data for 4 mice. Data is plotted as fold increase of luminescence intensity compared with day 0 (mean±SD). To assess, in vitro, whether CAR-PSCA T cells could eliminate CAPAN1 (GFP+) cells, a 72-hr co-culture experiment was performed at a 5:1 E:T ratio, with NT T cells serving as controls. b shows the percentage of residual tumor cells, as quantified using flow cytometry and gating on GFP+ cells and results are reported as mean±SD (n=4). (c) To assess whether CAPAN1 cells that were resistant to initial CAR-PSCA T cell treatment could be killed upon subsequent re-treatment, a subsequent co-culture was performed using either CAPAN1 cells initially treated with NT T cells (left panel) or those treated with CAR-PSCA T cells (right panel) as targets (E:T 5:1). After 72-hours residual tumor cells were again quantified by flow. Data is reported as the mean±SD; n=4. (d) To determine the mechanism of tumor resistance to T cell treatment, IHC analysis of CAPAN1 cells was performed only or post NT or CAR-PSCA T cell treatment. After exposure to control NT T cells tumor cells express both MUC1 and PSCA, whereas the majority of tumor cells treated with CAR-PSCA T cells have lost or express only low levels of PSCA antigen while retaining expression of MUC1.
Figure 2:
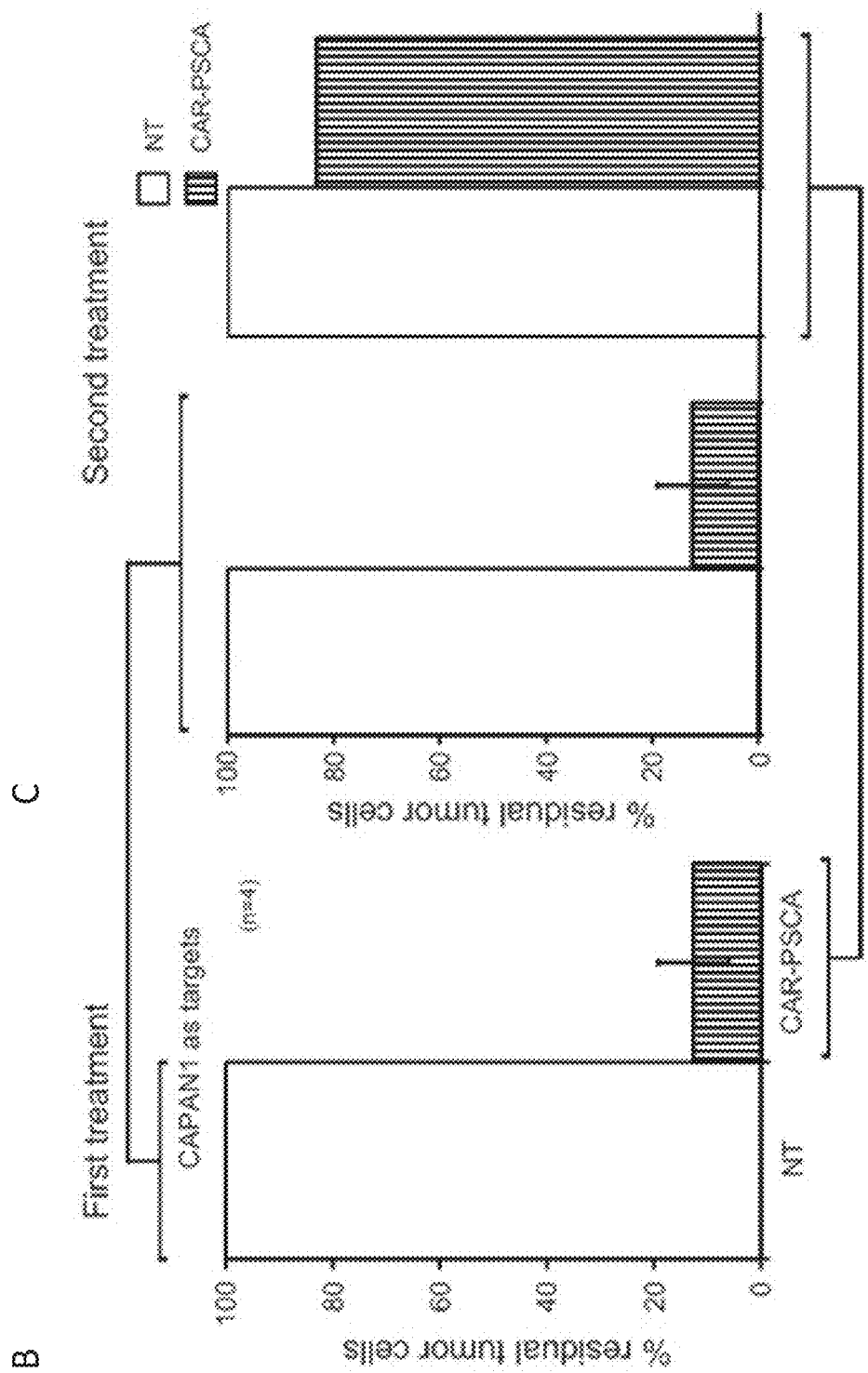
Figure 2:
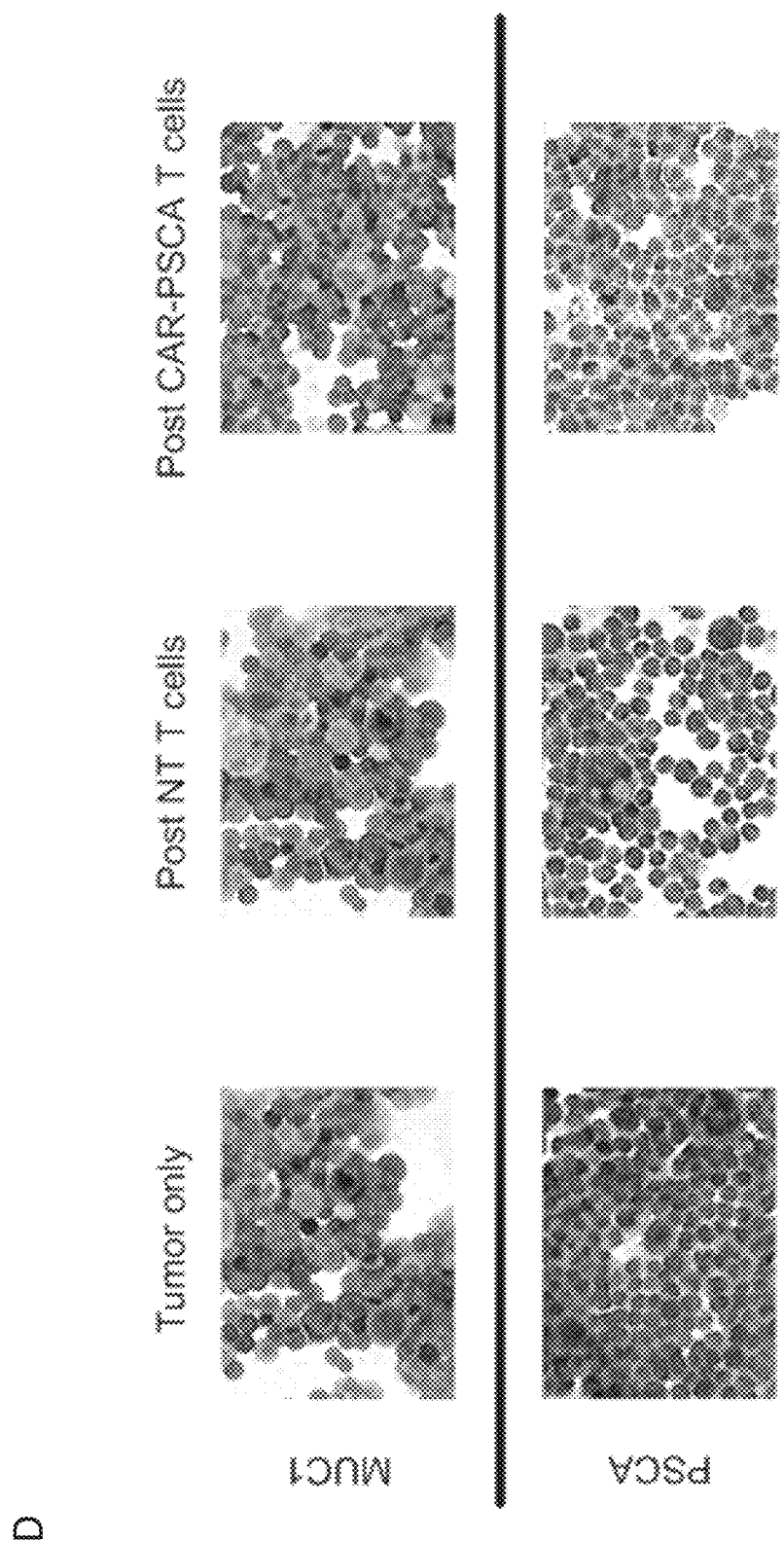

Targeting a Heterogeneous Tumor Using a Monospecific CAR-T Cell Product Selects Immune Escape Variants To determine whether CAR-PSCA T cell treatment could produce tumor elimination in vivo, SCID mice were engrafted with 1×10$^6$ CAPAN1 cells (a human pancreatic cancer cell line), which naturally express PSCA, and were modified with a γ-retroviral vector encoding eGFP-Firefly luciferase (CAPAN1-eGFP-FFLuc) to allow for in vivo bioluminescence detection. Once the tumor was established, as confirmed by an increase in the bioluminescence signal on two consecutive occasions, mice received a single infusion of either NT or CAR-PSCA T cells (30×10$^6$ cells). As shown in FIG. 2a CAR-PSCA T cell treatment resulted in an initial anti-tumor response (day 28 post-treatment), this was followed by a rapid tumor progression which by days 42 and 56 post-treatment was similar between the two groups (FIG. 2a, right panel).

To further investigate the reason for this immune escape, this phenomenon was modeled in vitro by co-culturing NT or CAR-PSCA T cells with CAPAN1-eGFP-FFLuc cells at a 5:1 ratio. After 72 hrs residual viable tumor cells were quantified by flow cytometry, gating on GFP+ cells, while T cells were excluded by co-staining with a CD3-directed antibody. Similar to the in vivo findings, while co-culture of NT T cells with the CAPAN1 cells had no impact on tumor cell growth, CAR-PSCA T cell treatment resulted in an initial anti-tumor response, reflected by a 82±9% reduction in tumor cell numbers (FIG. 2b). However, the tumor population that survived initial CAR-T cell exposure was resistant to re-treatment, as shown in FIG. 2c, unlike tumor cells that were originally treated with NT T cells, which retained their sensitivity to CAR-PSCA T cell treatment.

To determine the mechanism of resistance, IHC analysis was performed on tumor cells that had received a single treatment with either NT or CAR-PSCA T cells. As shown in FIG. 2d, while CAR-PSCA T cells eliminated CAPAN1 cells expressing high levels of PSCA antigen, a residual PSCA low/negative subpopulation remained, which subsequently outgrew. These residual tumor cells did, however, continue to express a second, untargeted, TAA, MUC1 (FIG. 2d).

Example 4

Figure 7:
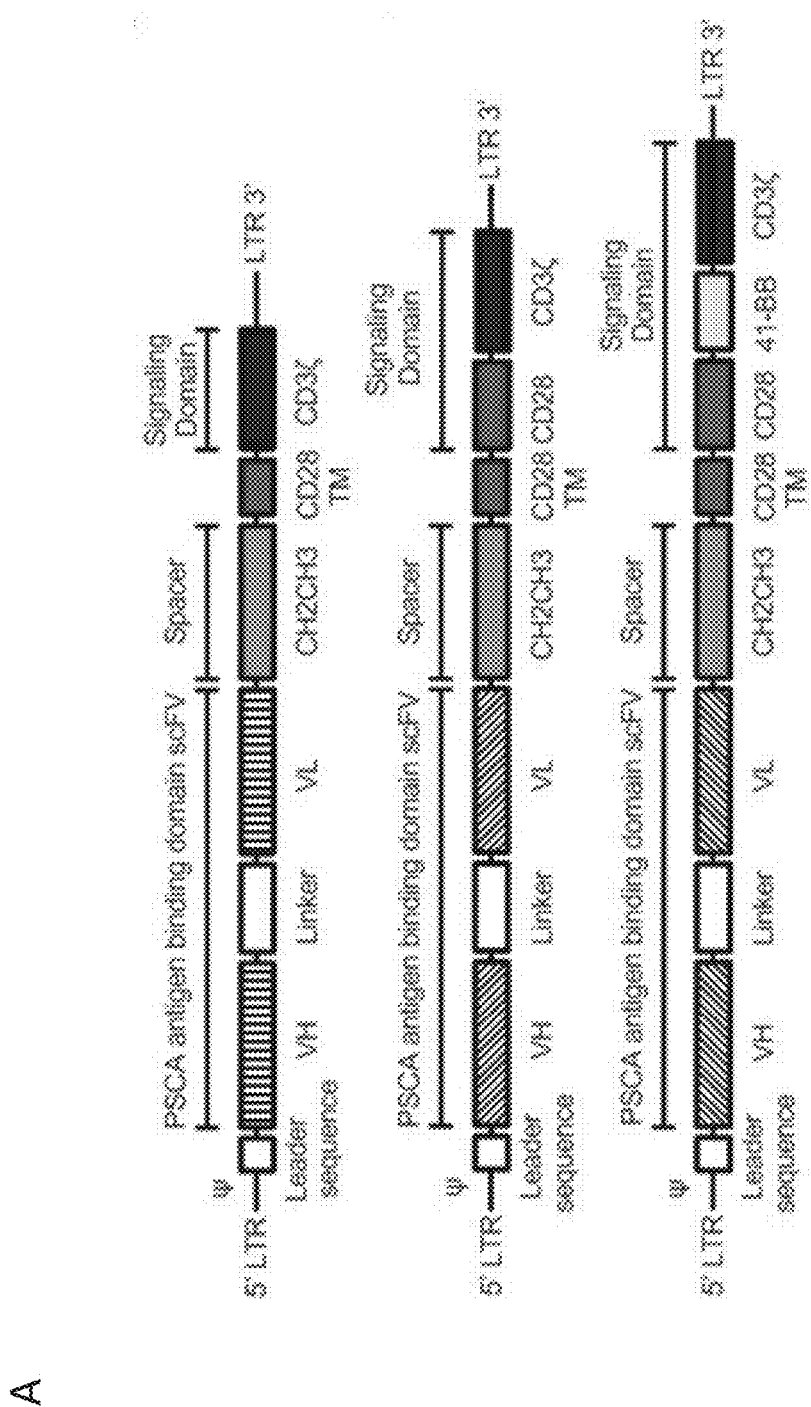
FIG. 7 shows that tumor immune escape occurs irrespective of whether T cells are modified with a $1^{st}$, $2^{nd}$ or $3^{rd}$ generation CAR construct. (a) retroviral vector maps of $1^{st}$, $2^{nd}$ and $3^{rd}$ generation CAR-PSCA constructs and (b) representative data confirming that all 3 generations of CARs can be expressed on T cells, as measured by flow cytometry (c) fold expansion of $1^{st}$, $2^{nd}$ and $3^{rd}$ generation CAR-PSCA modified T cells in a representative donor after co-culture with PSCA-expressing K562 cells at 2:1 T cell:K562 cell ratio. (d) T cells modified with $1^{st}$ $2^{nd}$ and $3^{rd}$ generation CARs show equivalent recognition of PSCA+ targets as assessed by a 6-hr cytotoxicity assay using 293T and CAPAN1 cells as targets (data is presented as % specific lysis at an E:T 10:1 for one representative donor as well as a 72-hour co-culture experiment performed at an E:T of 5:1, n=1, (e) where residual tumor cells were quantified by flow, gating on GFP+ cells.
Figure 7:
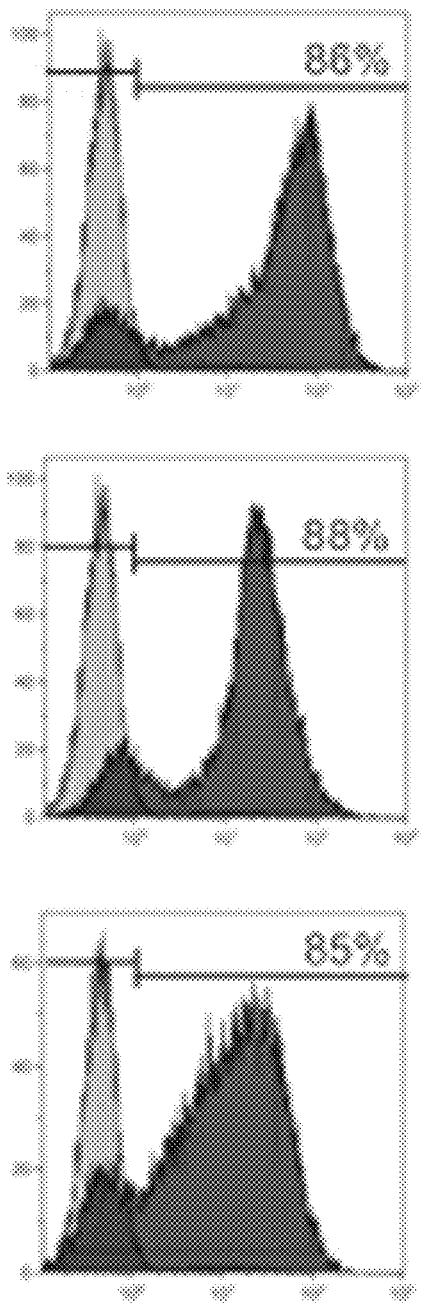
Figure 7:
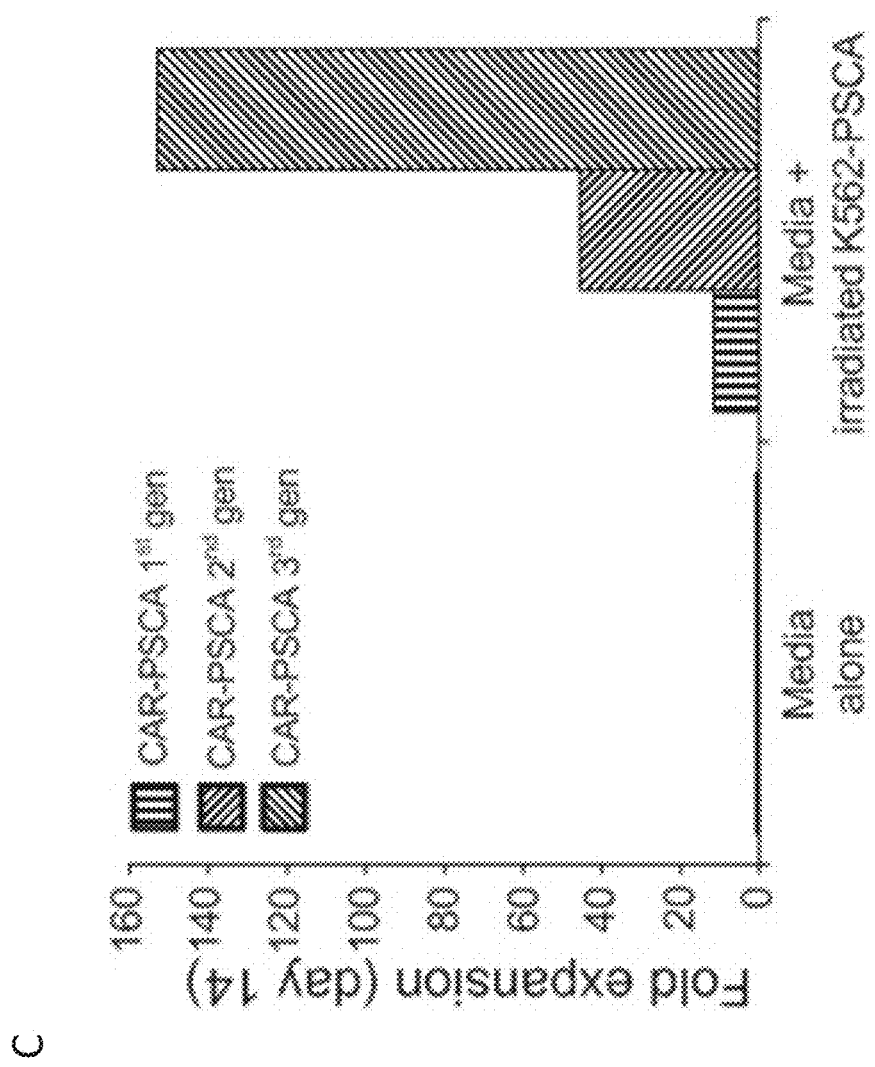
Figure 7:
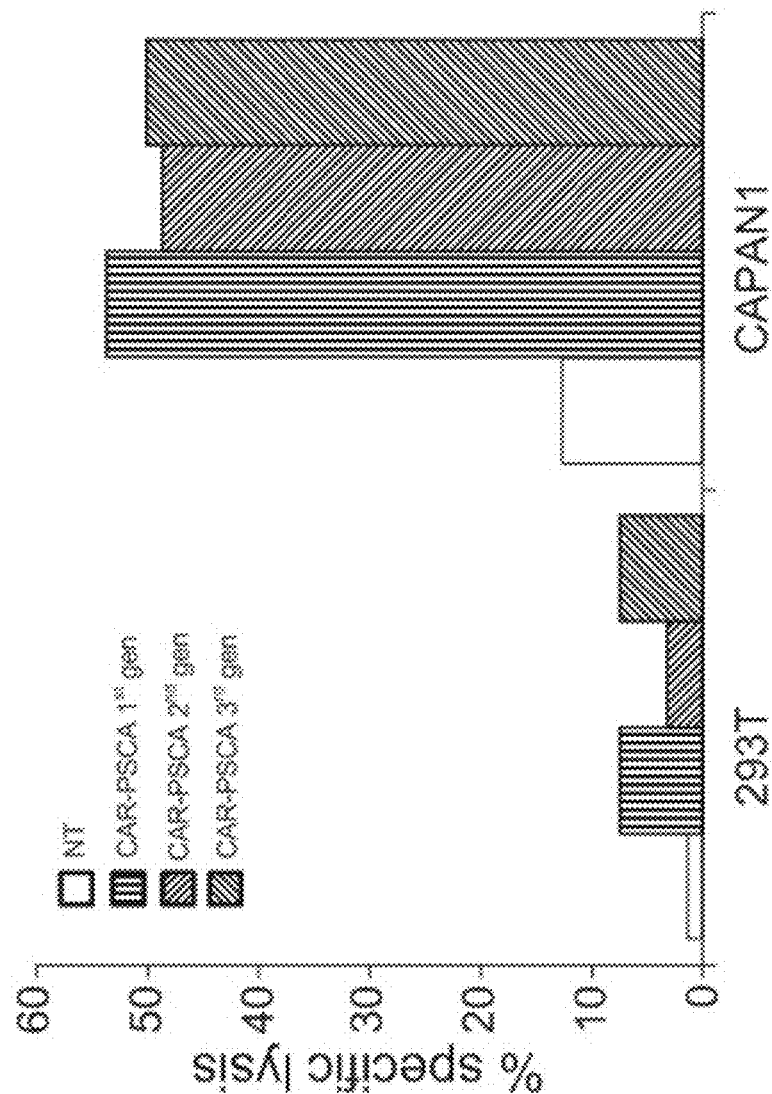
Figure 7:
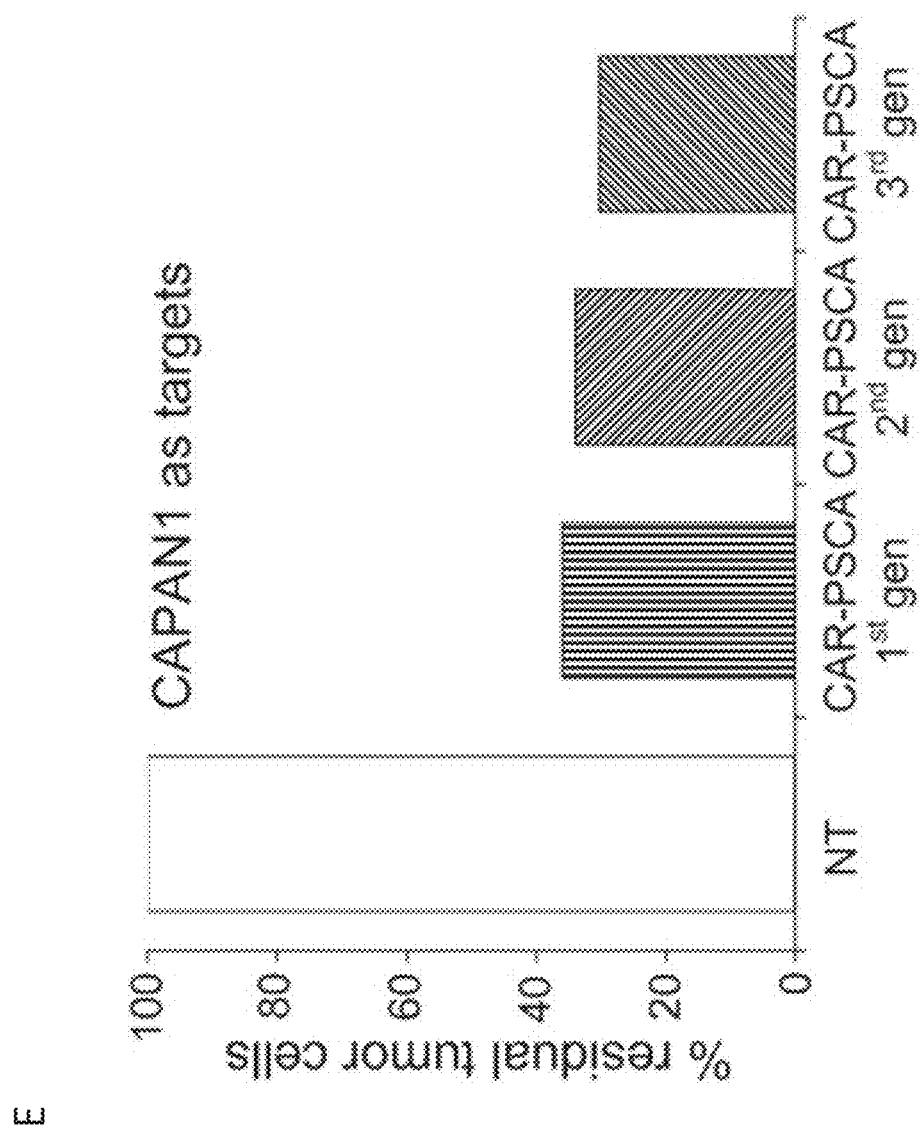

Tumor Immune Escape Occurs Even Using T Cells Modified to Express a $2^{nd}$ or $3^{rd}$ Generation CAR Recent reports have shown that T cells modified to express CARs containing co-stimulatory endodomains ($2^{nd}$ and $3^{rd}$ generation CARs) have increased proliferation, cytokine production and prolonged in vivo persistence. To test the hypothesis that more rapid or complete killing of cells expressing low levels of target antigen might prevent emergence of tumor escape variants, and to discover whether tumor immune escape could also be prevented using a later generation CAR construct, a CAR targeting PSCA was made that incorporated CD28 ($2^{nd}$ generation) or CD28+41BB ($3^{rd}$ generation) co-stimulatory endodomains. FIG. 7a shows the $1^{st}$, $2^{nd}$ and $3^{rd}$ generation CAR-PSCA retroviral vector maps and FIG. 7b shows expression of each in transduced primary T cells. T cells expressing both $2^{nd}$ and $3^{rd}$ generation CAR constructs proliferated more than the $1^{st}$ generation construct when cultured with K562 cells modified to express PSCA antigen (FIG. 7c), but all had equivalent cytolytic activity against CAPAN1 cells in both short-term (6 hr) $^{51}$Cr release (FIG. 7d) and long term (72 hr) co-culture assays (FIG. 7e), leaving behind the same residual resistant tumor subpopulation.

Example 5

Figure 3:
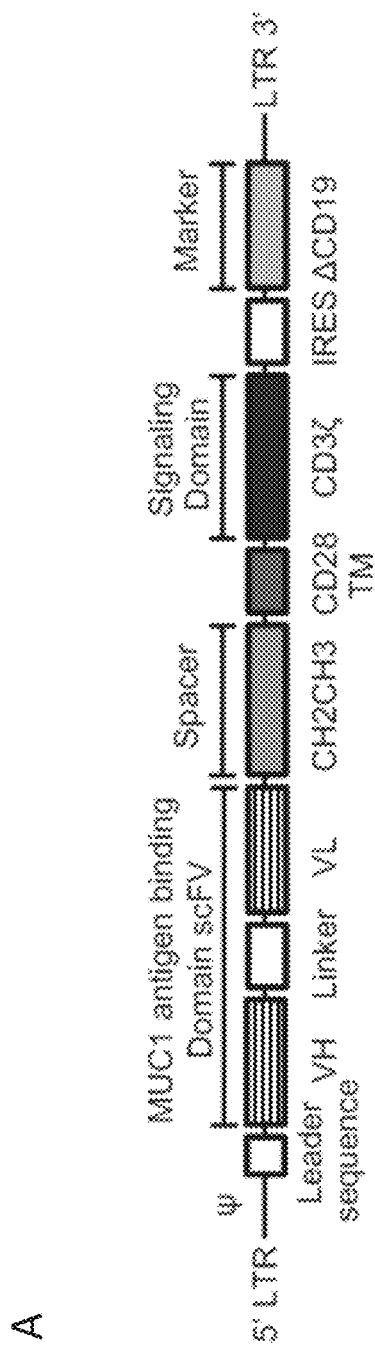
FIG. 3 demonstrates CAR-T cells modified to recognize MUC1 kill MUC1+ tumor cells. (a) shows a retroviral vector map of a first generation MUC1-specific CAR co-expressing a truncated form of CD19 (ΔCD19), b (left panel) shows a dot plot show representing the percentage of transgenic (CH2CH3 and ΔCD19 double-positive cells) in a representative donor, while the right panel shows summary data for 7 donors, (mean±SD). c shows the T cell phenotype of NT and CAR-MUC1 T cells (n=7). d shows in a 6-hr cytotoxicity assay, that CAR-MUC1 T cells can specifically kill MUC1+ targets (CAPAN1) with no recognition of control (293T) targets. NT T cells were used as additional controls and the data presented shows % specific lysis at an E:T of 10:1 (mean±SD) for 5 donors.
Figure 3:
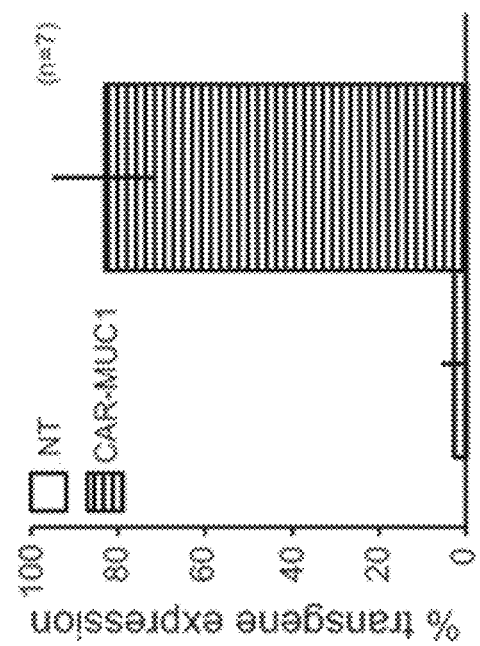
Figure 3:
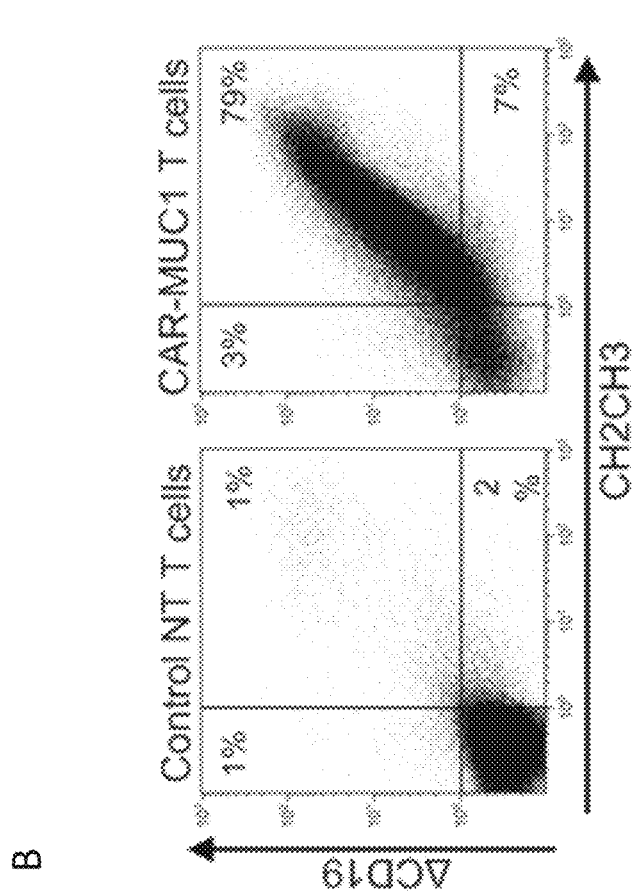
Figure 3:
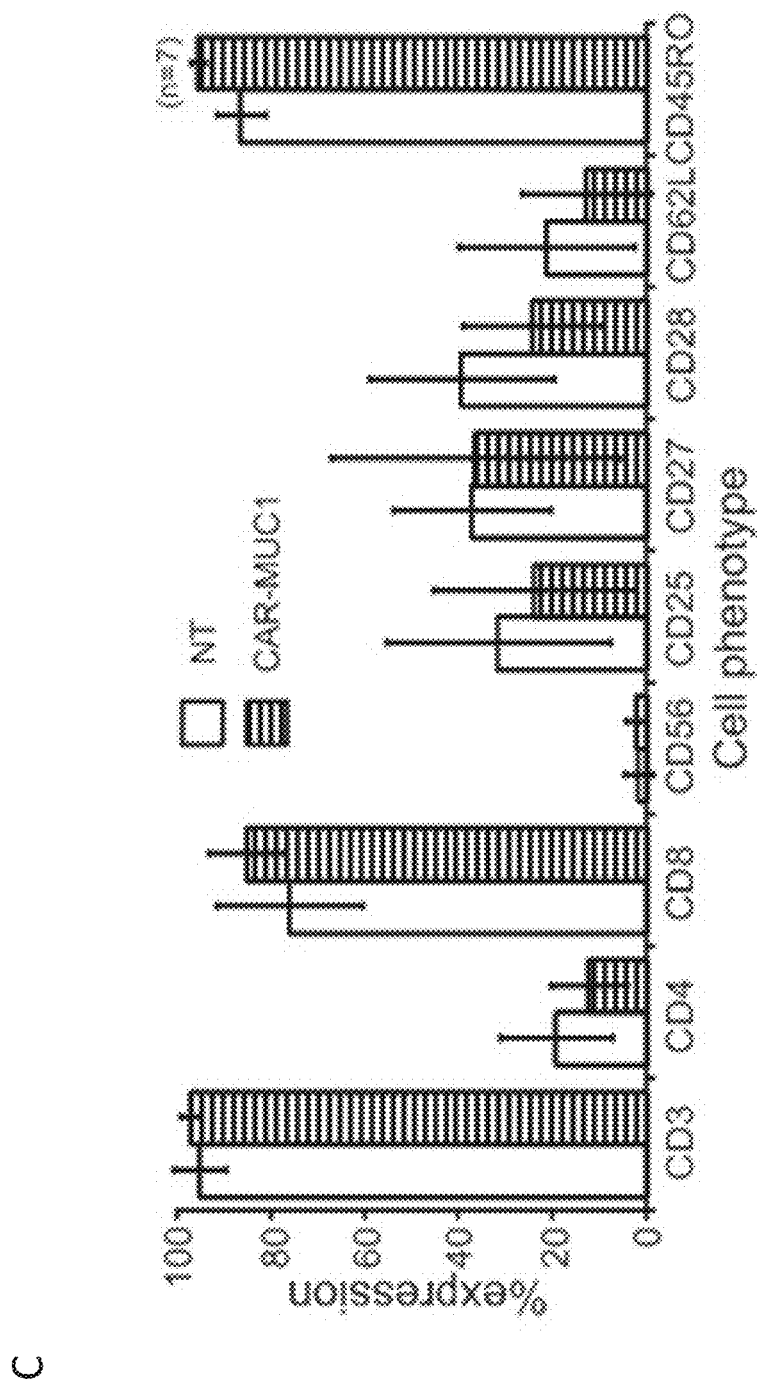
Figure 3:
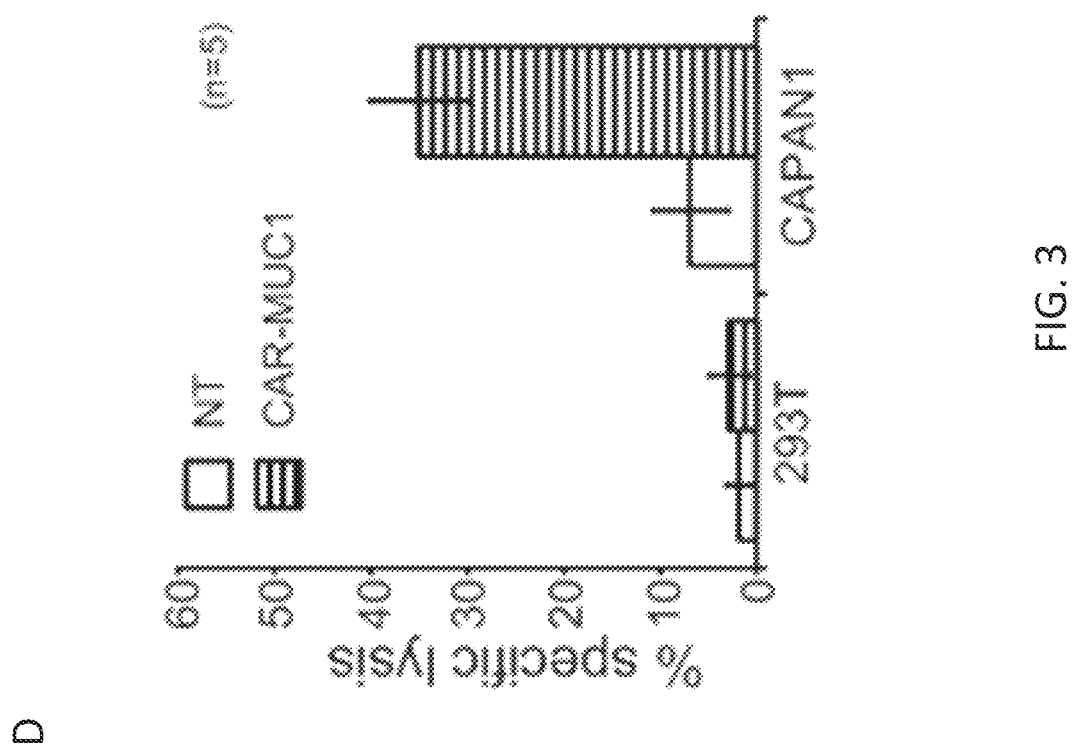

T Cells Modified with a CAR Targeting MUC1 Specifically Kill Antigen-Expressing Targets, but Tumor Heterogeneity Leads to Tumor Immune Escape Because heterogeneity of target antigen expression is an evident cause of tumor immune resistance and escape, it was next determined whether concomitant targeting of a second TAA, MUC1, would overcome this problem. A retroviral vector was generated encoding a CAR directed against MUC1, with a truncated CD19 molecule (ΔCD19) as a marker[17]. FIG. 3a shows the retroviral vector map. To test the activity of the MUC1-CAR T cells from 7 donors were transduced. FIG. 3b (left panel) shows detailed results from one representative donor, and summarized data for all 7 donors. The mean CAR-MUC1 expression was 83.1% (±11.5%) (FIG. 3b, right panel) and T cell phenotype was unaffected by CAR-transduction (FIG. 3c). Again, the cultures consisted predominantly of CD3+(95.2±5.7% and 97.2±2.0%) T cells, with CD4+(19.2±12.0% and 12.3±8.1%) and CD8+(76.1±15.5% and 85.1±8.3%) subpopulations (NT and CAR-MUC1 T cells, respectively), which expressed similar levels of the central memory markers CD62L, CD27, and CD45RO. CD56+ CD3− NK cells were a mean of 1.7% (±3.0%) of NT and 2.2% (±2.3%) of CAR-MUC1 T cells. Transgenic CAR-MUC1 T cells could specifically kill CAPAN1 cells, which naturally express MUC1 antigen (35±5% specific lysis at 10:1 E:T ratio), and had no activity against 293T cells, which are MUC1 negative targets (FIG. 3d).

Figure 4:
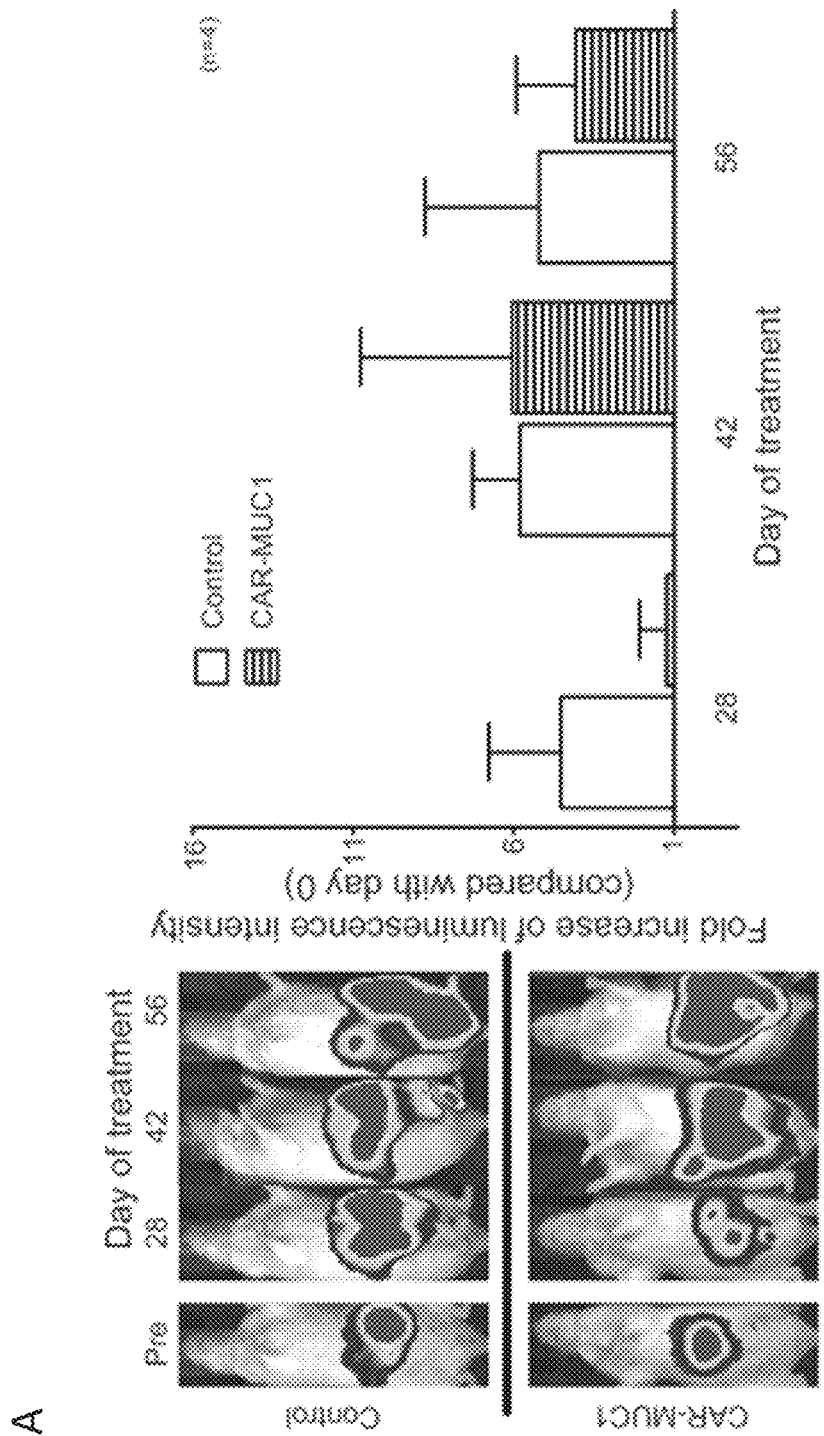
FIG. 4 provides that targeting a heterogeneous tumor with MUC1-specific CAR-T cells also leads to tumor immune escape. (a, left panel) shows bioluminescence images of representative mice engrafted with CAPAN-eGFP-FFluc intraperitoneally and administered either NT (top) or CAR-T cells (bottom). Imaging was performed prior to T cell infusion and at pre or 28, 42 or 56 days post-treatment. (A, right panel) shows summary data for 4 mice, with fold increase of luminescence intensity compared with day 0 plotted, (mean±SD). b shows that in an in vitro 72-hour co-culture assay not all CAPAN1/GFP-expressing cells are killed (n=3). Residual tumor cells were quantified by flow cytometry and gating on GFP and results are reported as mean residual tumor cells ±SD; (c) shows that while tumor cells originally treated with NT T cells are sensitive to retreatment with CAR-MUC1 T cells, those that were resistant to CAR-MUC1 T cells originally retained this resistance upon retreatment. Results represent data from a single donor using an E:T ratio of 5:1. (d) IHC of CAPAN1 cells treated with CAR-MUC1 T cells shows weak/intermittent MUC1 staining with no impact on the PSCA positive population.
Figure 4:
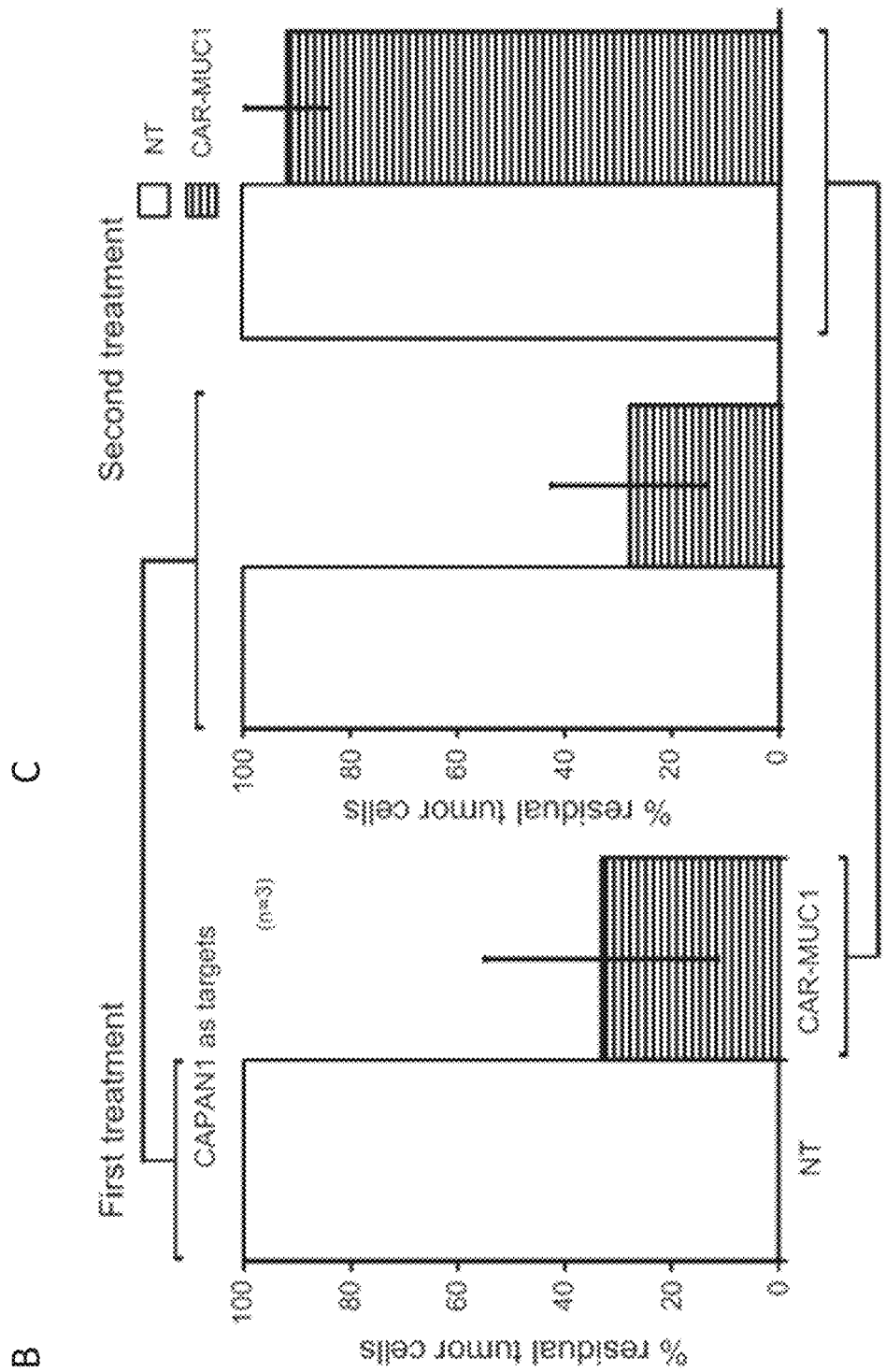
Figure 4:
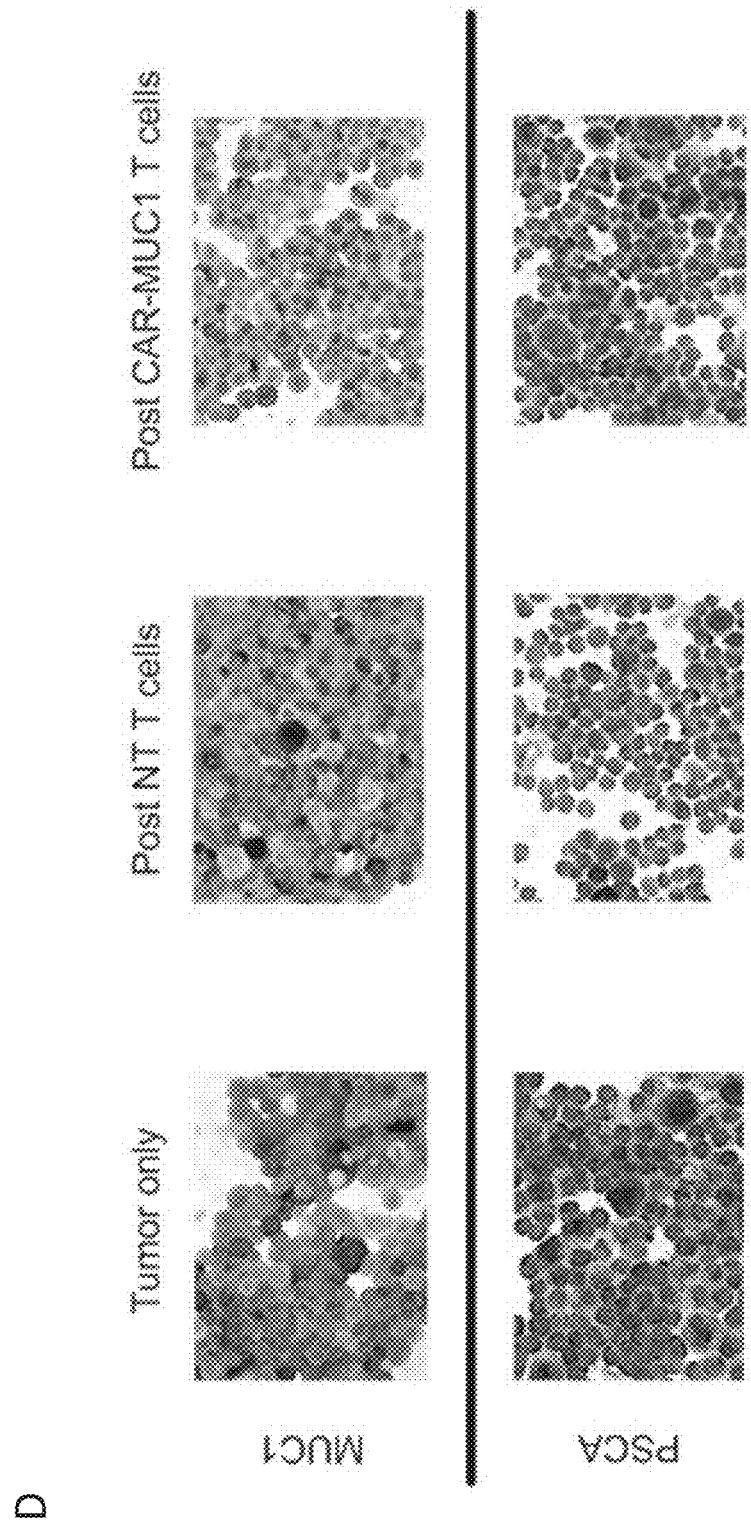

To determine whether CAR-MUC1 T cell monotherapy would also lead to tumor immune escape, SCID mice were again engrafted with the pancreatic cancer cells line CAPAN1-eGFP-FFLuc cells and treated with either NT or CAR-MUC1 T cells once the tumor was established. While CAR-T cell treatment produced an initial anti-tumor response measurable by a decrease in the tumor signal at day 28 post-treatment, this was followed by rapid tumor progression (FIG. 4a). To confirm that this escape was due to tumor antigen modulation NT or CAR-MUC1 T cells were co-cultured with CAPAN1-eGFP-FFLuc cells for 72 hrs and while CAR-MUC1 T cell treatment resulted in an initial reduction in tumor cells (66±21%) (FIG. 4b), those that remained proved insensitive to re-treatment (FIG. 4c), likely due to decreased antigen expression, as confirmed by IHC (FIG. 4d). These residual tumor cells did, however, continue to express the TAA PSCA.

Example 6

Figure 5:
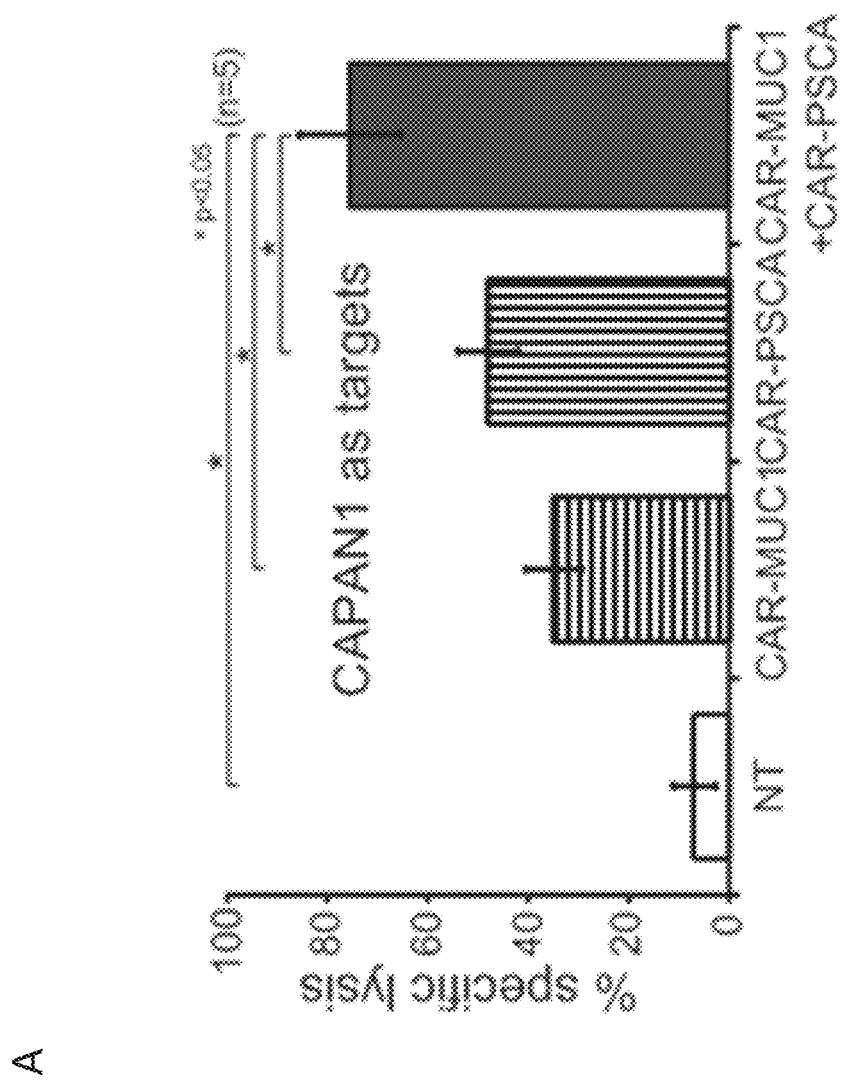
FIG. 5 shows that targeting tumors using a dual CAR approach produces superior antitumor activity. To determine whether combination therapy with CAR-MUC1 and CAR-PSCA T cells would produce superior anti-tumor effects, (a) a 6-hr cytotoxicity assays of NT, CAR-MUC1, CAR-PSCA or the combination with CAPAN1 cells as targets was performed. Results are expressed as % specific lysis ±SD at an E:T of 10:1 (n=5). Where indicated *, the P value was less than 0.05 using student t test. (b) also performed was a 72-hour co-culture study with the same panel of effectors and targets (E:T of 5:1, n=5). Residual tumor cells were quantified by gating on GFP+ cells and results are expressed as % residual tumor cells ±SD. It was next assessed whether the combination of CAR-MUC1 and CAR-PSCA T cells could control CAPAN1 tumor growth in vivo in SCID mice. (c) shows bioluminescence images of representative mice engrafted with CAPAN-eGFP-FFluc and treated with NT, CAR-MUC1, CAR-PSCA or the combination, while (d) shows summary results for the NT and dual-targeted groups (n=4) at pre or 28, 42, 56 or 63 days post treatment. Data is plotted as fold increase of luminescence intensity compared with day 0, (mean±SD).
Figure 5:
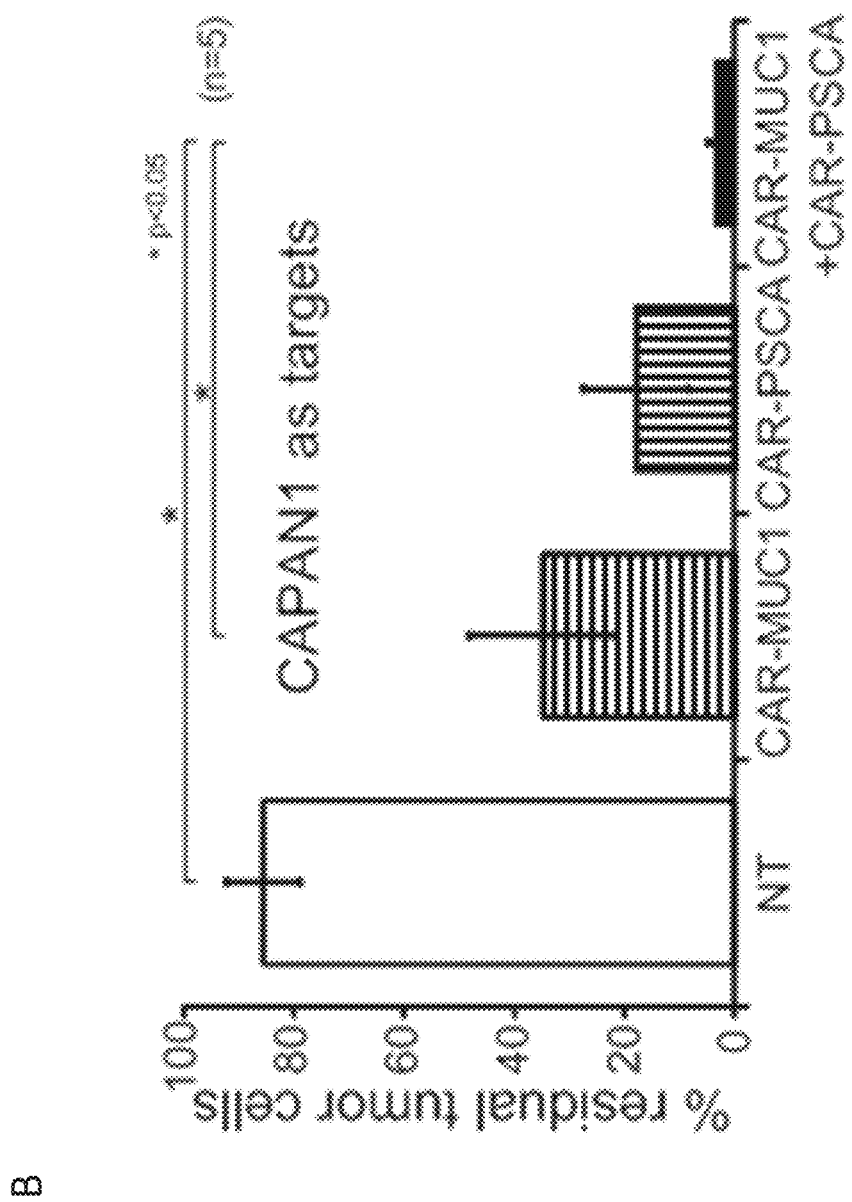
Figure 5:
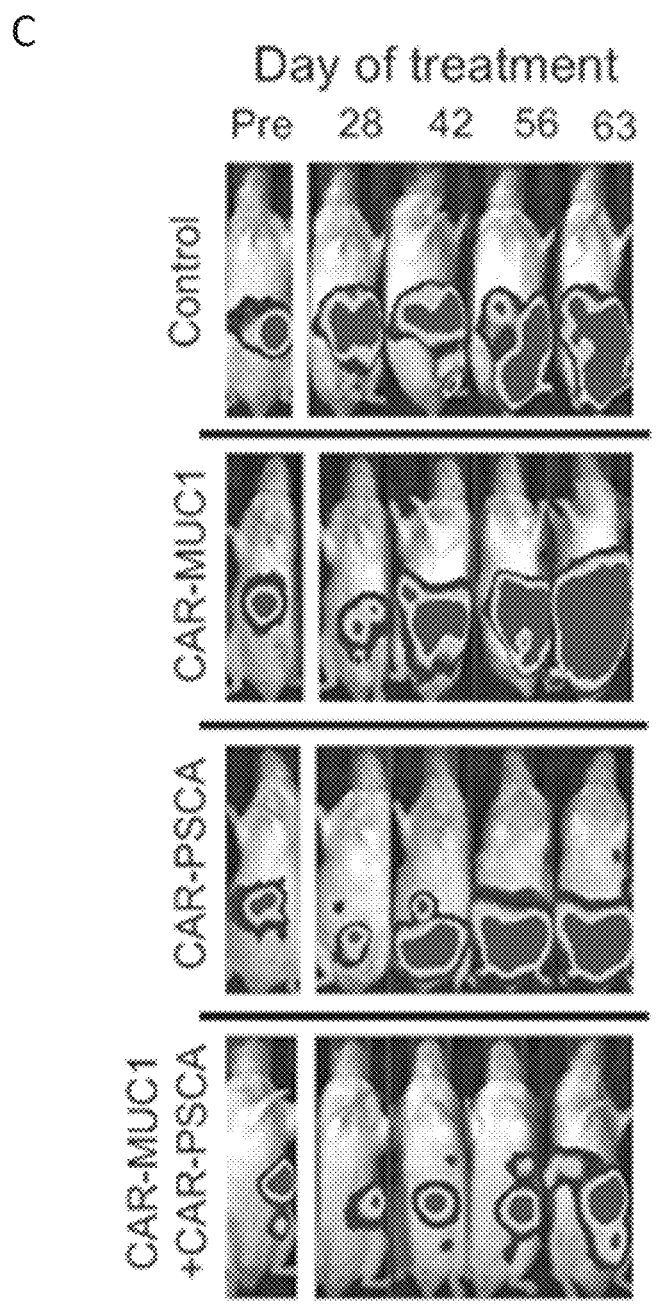
Figure 5:
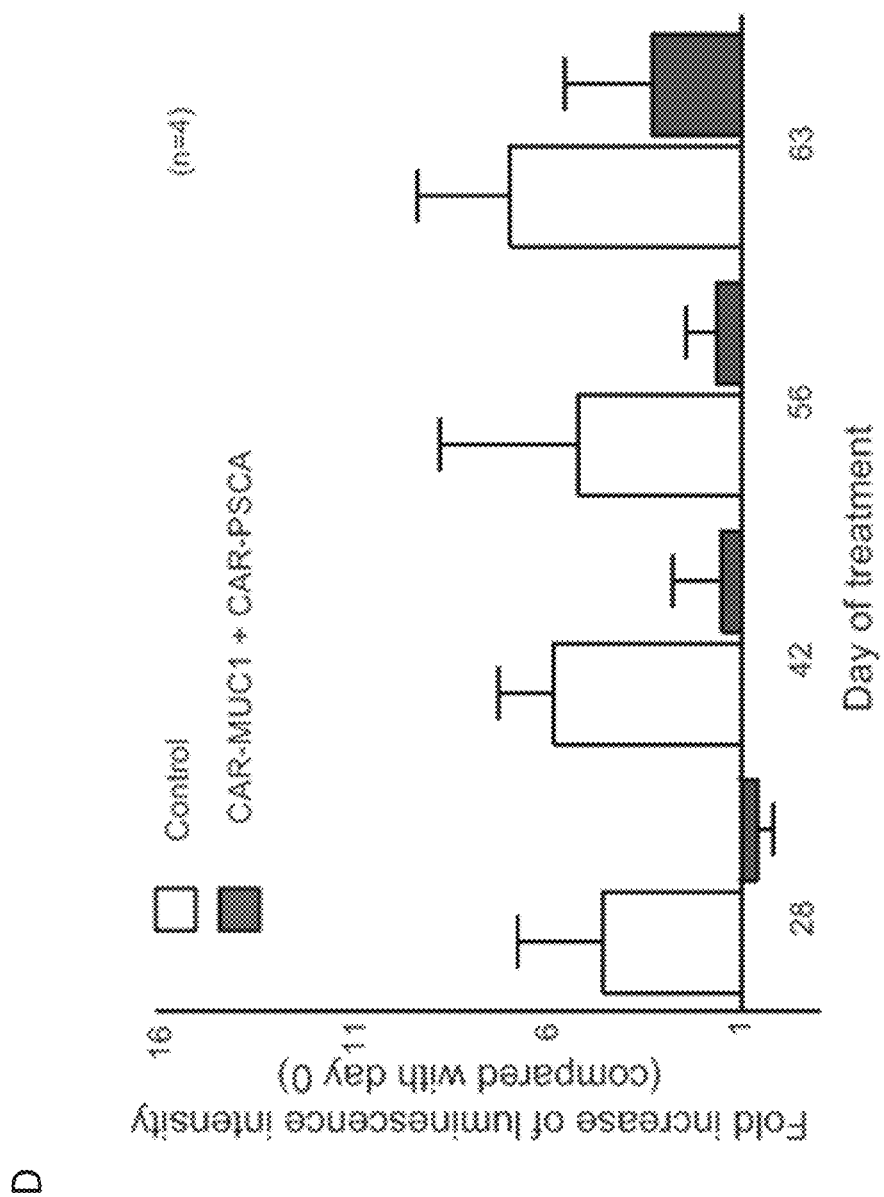

Combination of Car-T Cells Targeting Two TAAs Produces Superior Anti-Tumor Activity To determine whether dual-targeted CAR therapy would produce superior anti-tumor effects, the pancreatic cancer cells line CAPAN1 that naturally express both PSCA and MUC1, were cultured with both CAR-PSCA and CAR-MUC1 T cells simultaneously. In a short-term (6 hr) cytotoxicity assay, combination therapy produced superior tumor cell killing (75±8% specific lysis, E:T 10:1) compared to single antigen-specific T cells (35±5% and 48±6% specific lysis, E:T 10:1, CAR-MUC1 and CAR-PSCA, respectively) (FIG. 5a). Similar results were obtained after a 3-day co-culture, in which treatment with CAR-MUC1 T cells alone reduced tumor cells by 65±13%, treatment with CAR-PSCA T cells alone eliminated 82.1±9% of tumor cells, while dual targeted therapy was superior, resulting in a 96.6±1% reduction (FIG. 5b).

To address whether dual CAR-targeted therapy could result in tumor elimination, SCID mice were engrafted with CAPAN1-eGFP-FFluc cells. As shown in FIGS. 5c and 5d, treatment with a combination of CAR-MUC1 and CAR-PSCA T cells produced superior anti-tumor effects compared with either tested individually. However, this effect was not sustained and by day 63 the tumor recurred in all animals. Thus, dual targeted therapy was also insufficient to eliminate all cancer cells.

Example 7

Generation of an Artificial System to Model Tumor Immune Escape

Figure 6:
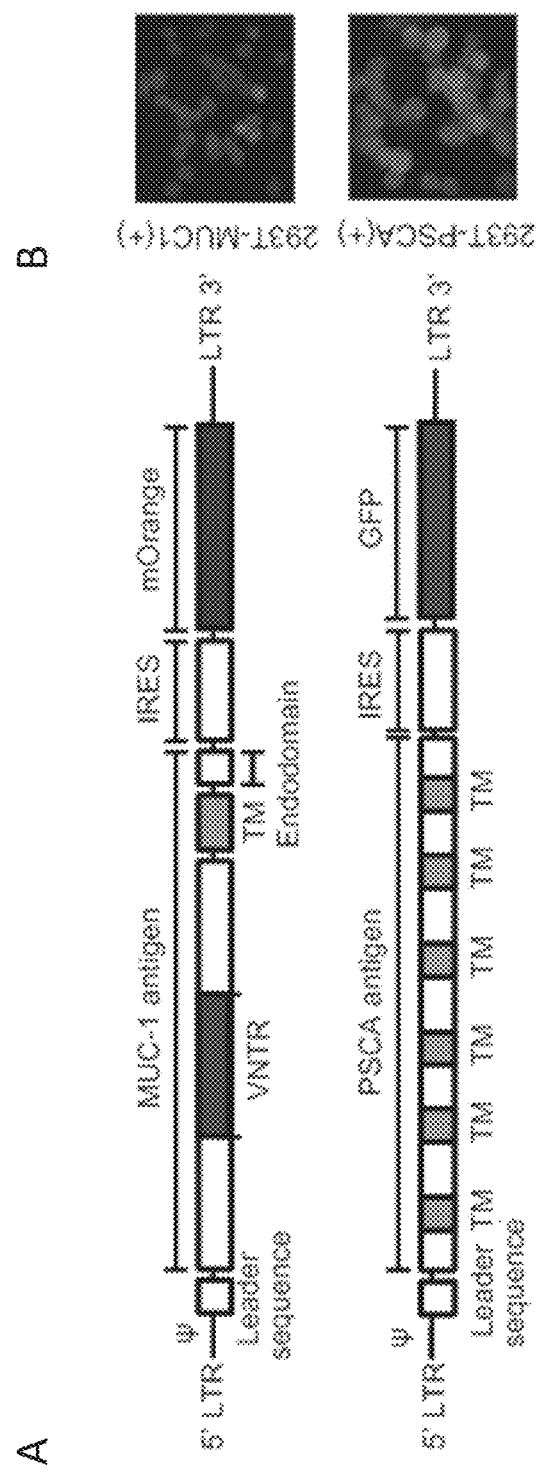
FIG. 6 demonstrates characterizing the tumor immune escape phenomenon using an artificial tumor model. (a) shows two retroviral vector maps, the first encoding the TAA MUC1, which has a variable number of proline-rich segments that are tandemly repeated (variable number tandem repeat; VNTR)[37] and co-expressing mOrange. The second encodes the TAA PSCA, which contains six transmembrane portions, and co-expressing GFP. (b) shows immunofluorescence staining for MUC1/mOrange and PSCA/GFP in transduced 293T cells, (c) shows a 72-hour co-culture experiment where a mixture of 293T expressing MUC1/mOrange and 293T expressing PSACA/GFP (1:1 ratio) with incubated with either NT or CAR-PSCA T cells at an E:T 10:1 (n=6). Residual tumor cells were quantified by gating on GFP+ and mOrange+ populations and results are expressed as % residual tumor cells ±SD. (d) the frequency of detectable tumor cells are quantified at co-culture initiation (0), then at 12, 24, 36, 48 and 60 hours after treatment with CAR-PSCA T cells (n=6), and distinguished based on expression of either GFP or mOrange. Results are expressed as % residual tumor cells. (e) To determine whether the intensity of antigen expression correlated with sensitivity to T cell treated the fluorescence intensity of GFP was measured at co-culture initiation (0), then at 12, 24, 36, 48 and 60 hours after treatment with CAR-PSCA T cells, n=6. Results are presented as maximum fluorescence intensity ±SD, (f) shows a 72-hour co-culture experiment where a mixture of 293T expressing MUC1/mOrange and 293T expressing PSACA/GFP (1:1 ratio) with incubated with either NT or CAR-MUC1 T cells at an E:T 10:1 (n=5). Residual tumor cells were quantified by gating on GFP+ and mOrange+ populations and results are expressed as % residual tumor cells ±SD. (g) Tumor cells are quantified over time based on expression of either GFP or mOrange (n=5). Results are expressed as % residual tumor cells. (h) To determine whether the intensity of antigen expression correlated with sensitivity to T cell treated the fluorescence intensity of mOrange was measured at co-culture initiation (0), then at 12, 24, 36, 48 and 60 hours after treatment with CAR-MUC1 T cells, n=5. Results are presented as maximum fluorescence intensity ±SD. (i) shows a 72-hour co-culture experiment where a mixture of 293T cells expressing MUC1/mOrange and 293T expressing PSACA/GFP (1:1 ratio) were incubated with either NT or the combination of CAR-MUC1 and CAR-PSCA T cells at an E:T 10:1 (n=5). Residual tumor cells were quantified by gating on GFP+ and mOrange+ populations and results are expressed as % residual tumor cells ±SD. (j) Sensitivity of the tumor cells to dual CAR therapy is assessed at initiation (0), then at 12, 24, 36, 48 and 60 hours after treatment. Results are expressed as % residual tumor cells (n=5). (k) To determine whether the intensity of antigen expression correlated with sensitivity to T cell treated the fluorescence intensity of mOrange was measured at initiation (0), then at 12, 24, 36, 48 and 60 hours after treatment with the combination of CAR-MUC1 and CAR-PSCA T cells, n=5. Results are presented as maximum fluorescence intensity ±SD.
Figure 6:
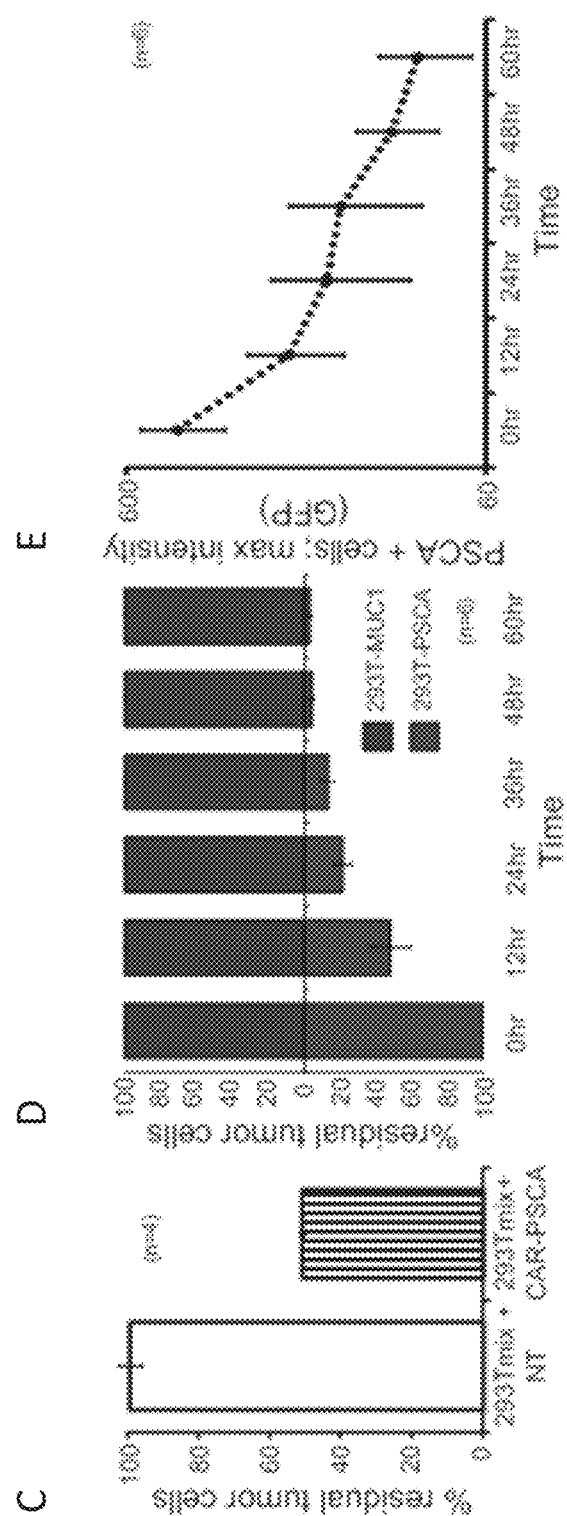
Figure 6:
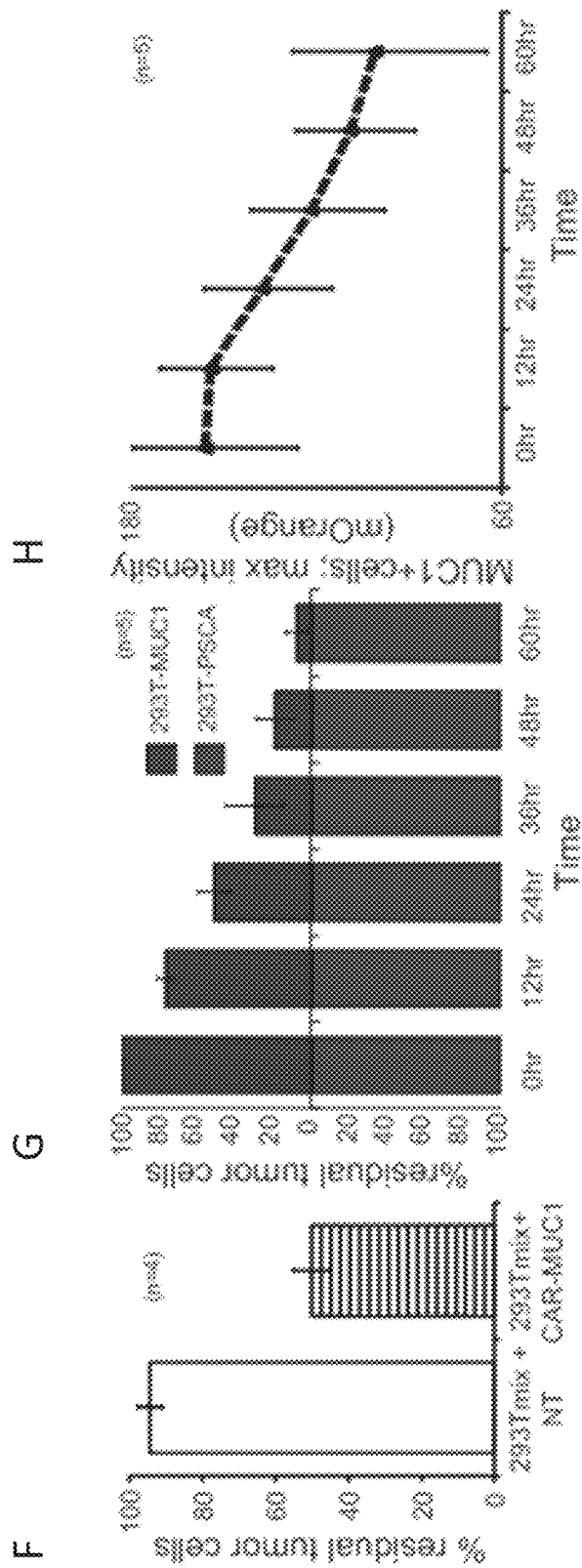
Figure 6:
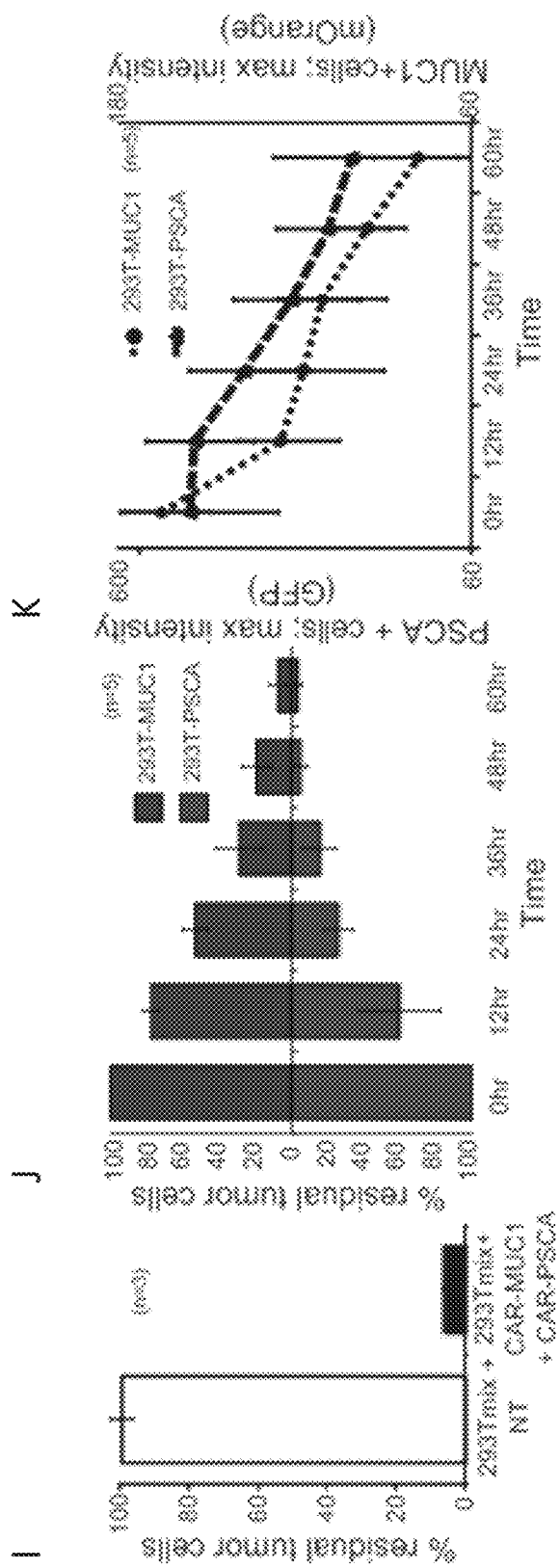
Figure 8:
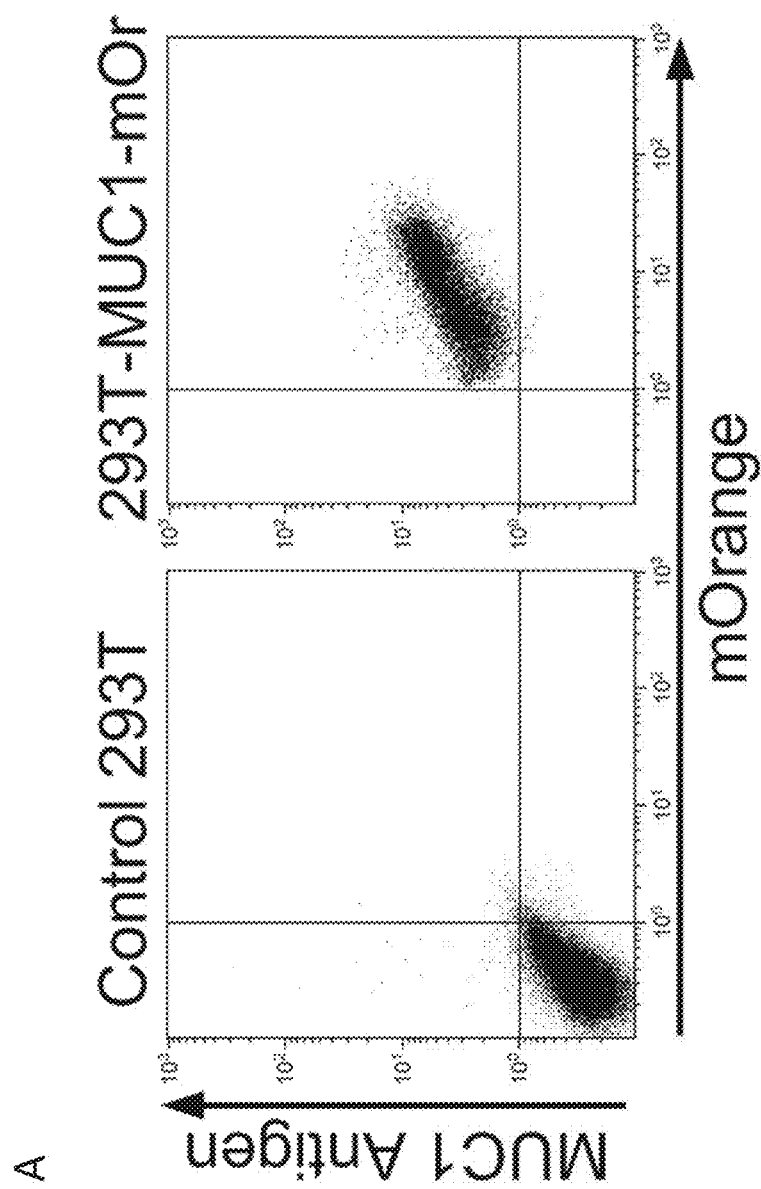
FIG. 8 demonstrates that fluorescence intensity of mOrange was correlated with MUC1 antigen expression on the engineered 293T cells expressing MUC1-mOrange. a shows a dot plot of the control 293T cells and the engineered 293T-MUC1-mOrange cells co-expressing MUC1 antigen and mOrange (MUC1 Ag and mOrange-double positive cells).

To better understand the mechanism behind this therapy failure, an engineered tumor model was developed by transgenically expressing either MUC1 or PSCA TAAs in 293T cells. Thus, two retroviral vectors were generated; the first encoding the MUC1 antigen and co-expressing the fluorescent tag mOrange and the second encoding the PSCA antigen and co-expressing GFP. The intensity of the fluorescent tag correlated with the intensity of antigen expression, as shown in FIG. 8 for MUC1, thus allowing us to monitor, in real time, the anti-tumor activity of our CAR-T cells. FIG. 6a shows the retroviral vector maps and FIG. 6b shows the expression of MUC1/mOrange and PSCA/GFP in 293T cells. To ensure that each tumor cell expressed a target antigen, these cells were subsequently sorted to achieve pure populations that were either 100% MUC1-expressing (mOrange+) or PSCA-expressing (GFP+).

To mimic a heterogeneous tumor population the sorted cells were mixed at a 1:1 ratio and initially treated with either NT or CAR-PSCA T cells for 72 hrs. NT T cell treatment had no impact on residual tumor cell numbers whereas treatment with CAR-PSCA T cells alone reduced the number of engineered tumor cells by 50.9±1% (FIG. 6c), reflecting a selective reduction in the GFP+ (PSCA-expressing) population (98.1±1%). To examine the kinetics of CAR-T cell killing tumor cell numbers were quantified, by flow cytometry, over time (0, 12, 24, 36, 48, and 60 hrs). As shown in FIG. 6d, there was a progressive decrease in the number of GFP+ tumor cells, which was most pronounced within the first 24 hrs post-treatment (45.4±11% reduction between 0-12 hrs and 29.7±4% reduction between 12-24 hrs), and less marked thereafter (10.7±4% from 24-36 hrs, 10.2±1% from 36-48 hrs, and 1±0.9% from 48-60 hrs). Nevertheless, a residual PSCA-expressing subpopulation (1.9%) remained. To next investigate whether sensitivity to CAR-mediated killing was linked to the intensity of target antigen expression on tumor cells, the fluorescence intensity of GFP was also measured at the same timepoints. As shown in FIG. 6e, tumor cells expressing the highest antigen levels were killed first, while those with lowest expression survived.

These studies were repeated but substituted with CAR-MUC1 T cells as the effector population. After 72 hrs CAR-MUC1 T cell treatment the total number of tumor cells had decreased by 49.9% (±5%) (FIG. 6f), representing a selective and gradual reduction in MUC1/mOrange+ tumor cells over time (FIG. 6g), until only MUC1 "low" tumor cells remained (FIG. 6h), while the PSCA+ population was unaffected.

Next, to determine whether dual-targeted CAR therapy would produce superior anti-tumor effects, the heterogeneous tumor cell population (1:1 mix of MUC1/mOrange+ and PSCA/GFP+ 293T cells) was co-cultured with both CAR-MUC1 and CAR-PSCA T cells. However, even this strategy failed to eliminate all tumor cells and after 72 hrs 6.0±3% of cells remained—3.9±2% residual MUC1/mOrange+ and 1.9±1% residual PSCA/GFP+ cells (FIG. 6i). Again, these residual subpopulations reflected cells with the lowest intensity of target antigen expression, judged by mOrange and GFP fluorescence (FIGS. 6j and 6k). Thus, sensitivity to CAR-T cell treatment is related to both the proportion of cells expressing the targeted antigen as well as the intensity at which the antigen is expressed.

Figure 9:
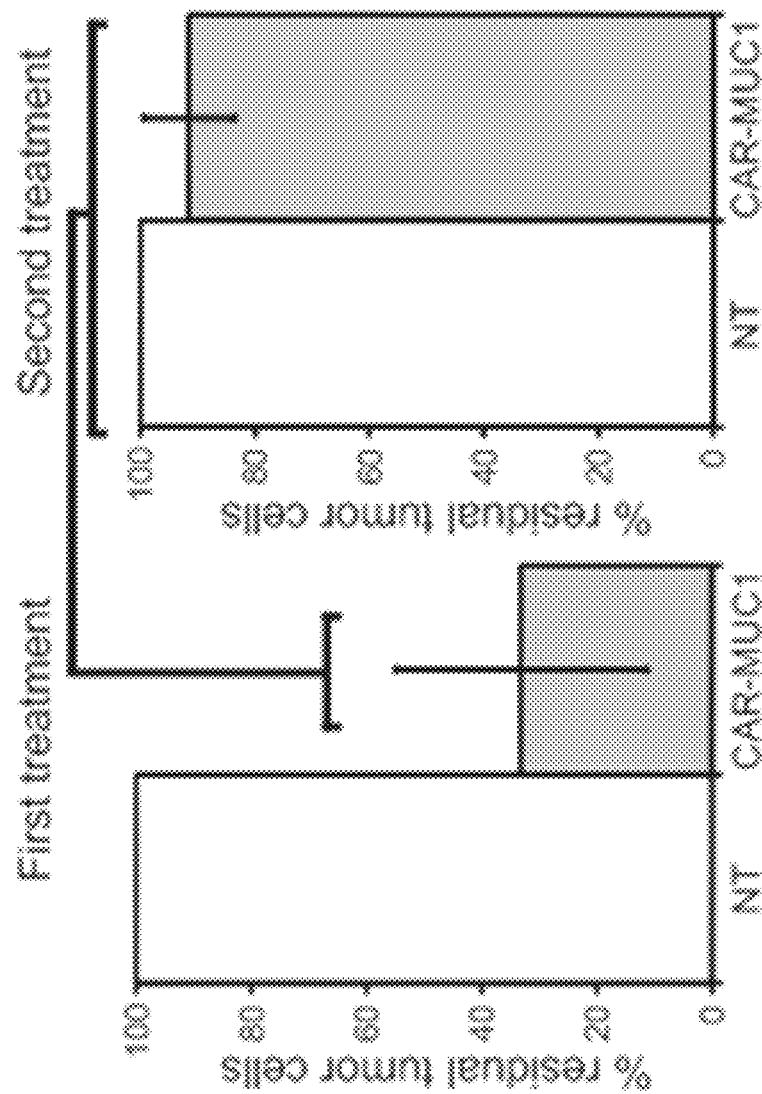
FIG. 9 shows that decitabine treatment upregulates MUC1 expression of CAR-resistant T cells and re-sensitizes them to T cell treatment. To assess whether CAPAN1 cells that were resistant to initial CAR-MUC1 T cell treatment could be killed upon subsequent re-treatment we performed a 72-hr co-culture experiment at a 5:1 E:T ratio, with NT T cells serving as controls. a (right panel) shows the percentage of residual tumor cells, as quantified using flow cytometry and gating on GFP+ cells and results are reported as mean±SD (n=4) then a subsequent co-culture (left panel) using CAPAN1 cells initially treated with CAR-MUC1 T cells as targets (E:T 5:1), after 72-hours residual tumor cells were again quantified by flow. Data is reported as the mean±SD; n=4. (b) To determine whether decitabine exposure would upregulate MUC1 expression in this resistant population we evaluated antigen expression, by flow, on CAR-resistant cells (grey histogram) and those cultured in decitabine (black histogram). To next assess whether decitabine treatment resensitized CAPAN1 cells to CAR-MUC1 T cells we performed a 72-hr co-culture experiment using CAPAN1 cells initially treated with CAR-MUC1 T cells (c) then either left untreated or cultured with decitabine as targets (E:T 5:1). After 72-hours retreatment with CAR-MUC1 T cells, residual tumor cells were again quantified by flow. Data is reported as the mean±SD; n=2.
Figure 9:
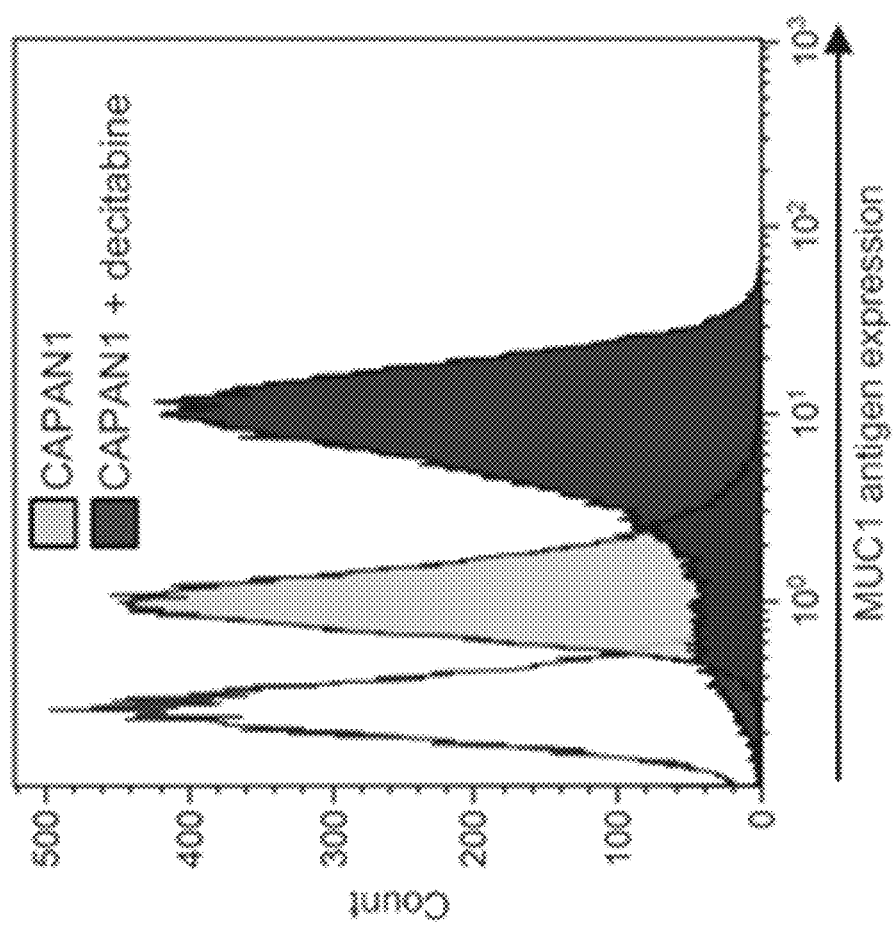
Figure 9:
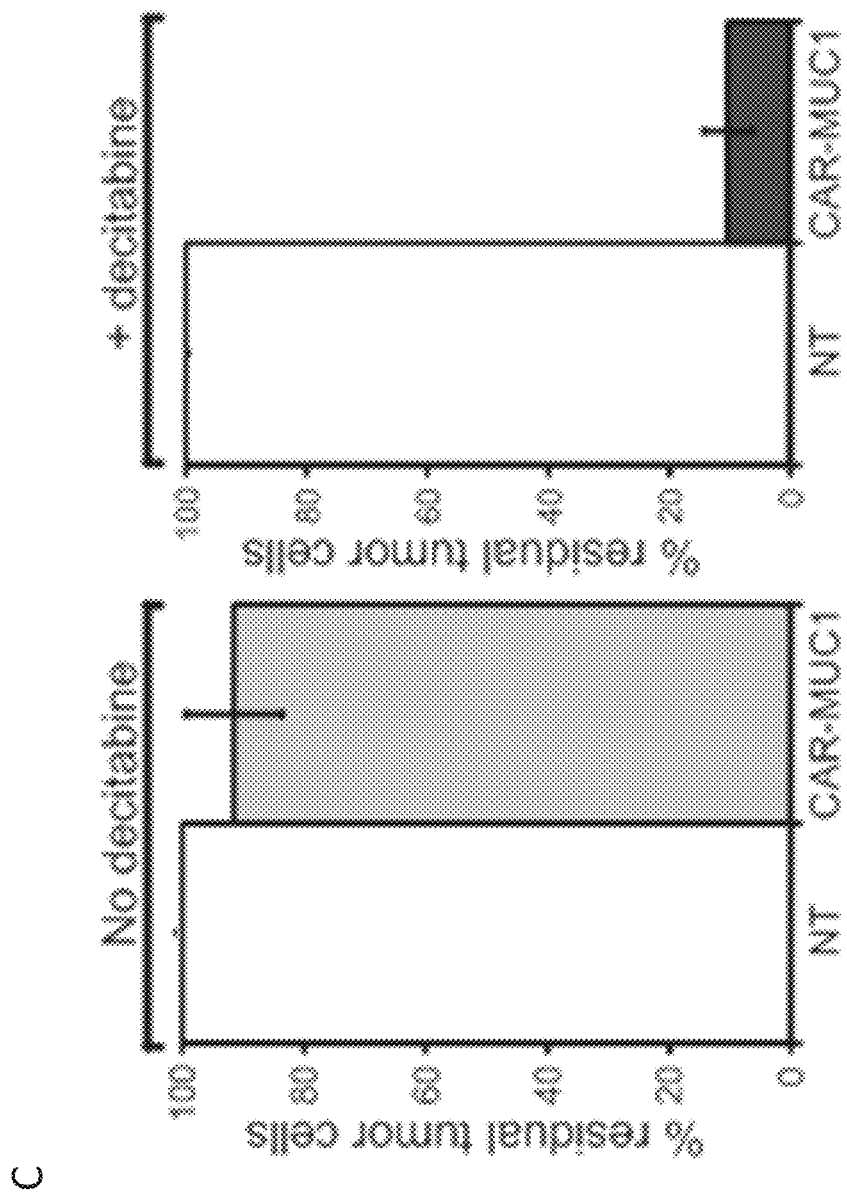

Finally, to determine whether CAR-T cell potency could be improved by combination with conventional epigenetic modulators, which can increase TAA expression by demethylating DNA, CAPAN1 cells were cultured that had been previously treated with CAR-MUC1 T cells and consequently expressed only low levels of the target antigen, with 1 μM of decitabine, a hypomethylating agent. Decitabine exposure resulted in an increase in the intensity of MUC1 expression from 3.5 to 26.0 (relative mean fluorescence intensity) after 4 days of treatment (FIGS. 9a and 9b), re-sensitizing previously resistant tumor cells to CAR-MUC1 T cell killing (FIG. 9c).

Example 8

Combining Car T-Cells with Epigenetic Modifiers

Figure 10:
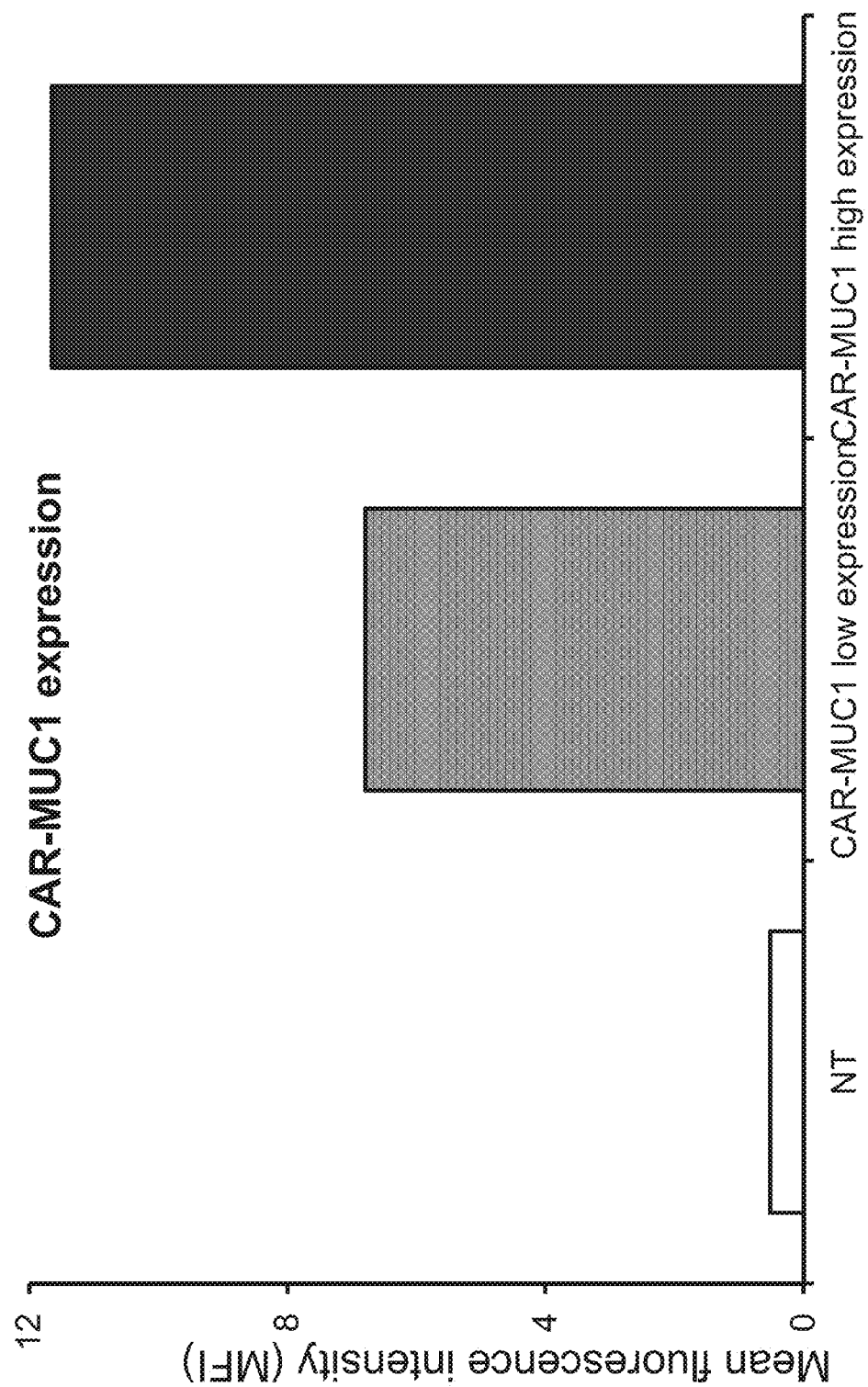
FIG. 10 shows exemplary expression of a CAR-MUC1 on T cells.

FIG. 10 represents expression of CAR-MUC1 on cells that were selected for high expressing cells or low expressing cells.

Figure 11:
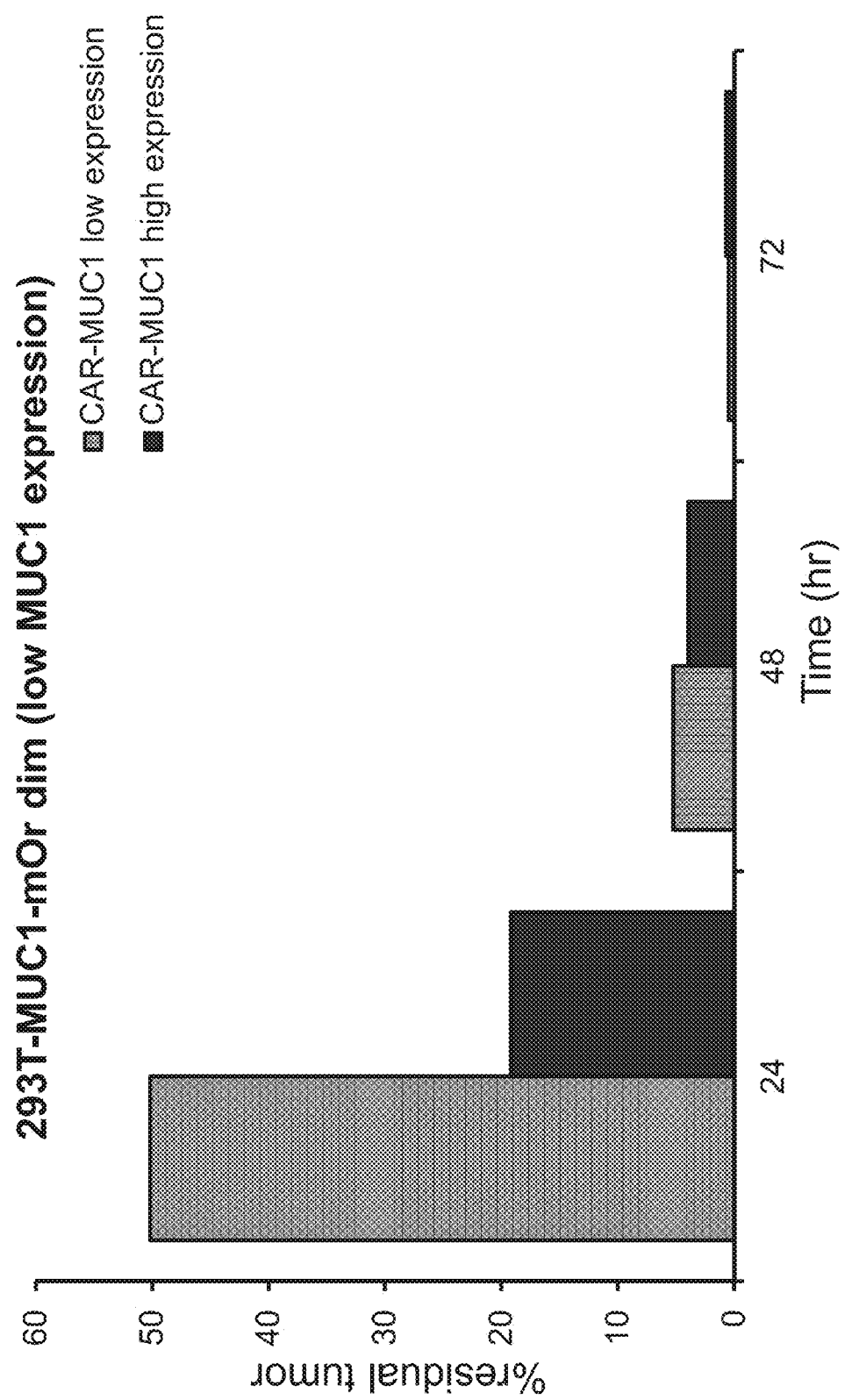
FIG. 11 shows that higher expression of CAR on modified-T cells has faster killing kinetics (293T-MUC1-mOr dim (low MUC1 expression)).
Figure 12:
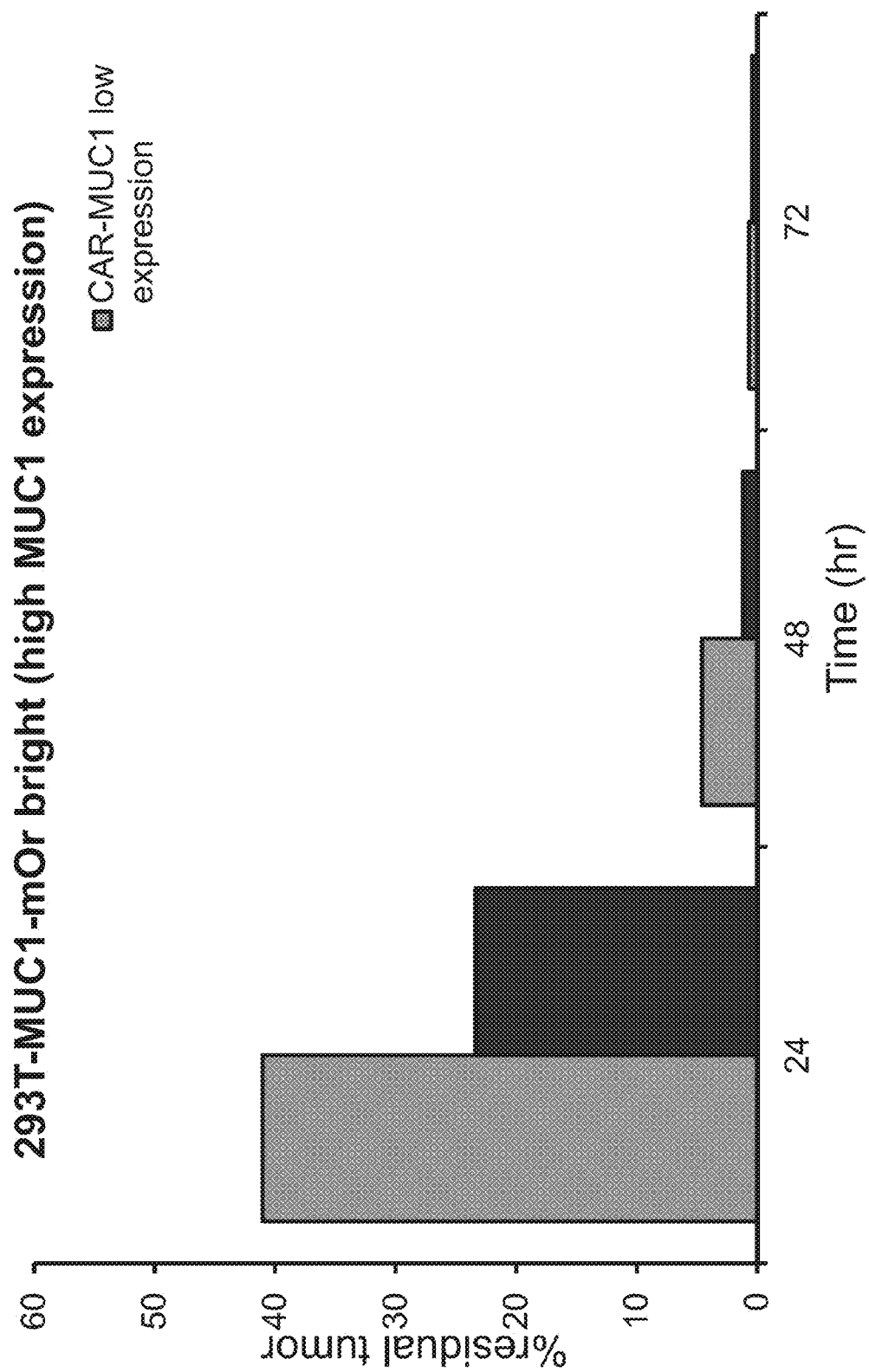
FIG. 12 demonstrates that higher expression of CAR on modified-T cells has faster killing kinetics. (293T-MUC1-mOr bright (high MUC1 expression)).

FIGS. 11 and 12 provide a comparison of the effectiveness of effector cells that have high or low expression of a CAR compared to tumor cells that express high or low levels of the antigen to which the CAR is targeted.

In FIG. 11, cells with either low expression of CAR-MUC1 or high expression of CAR-MUC1 are examined for antitumor properties by assaying for percentage of residual tumor cells that express the target antigen at a low level. Twenty four hours after exposure of the CAR-MUC1 T cells to the tumor cells, those CAR-MUC1 T cells having high expression of the CAR are more effective than those CAR-MUC1 T cells having low expression of the CAR in eliminating the tumor cells that have low expression of the MUC1 antigen.

In FIG. 12, there is an analogous assay in which cells with either low expression of CAR-MUC1 or high expression of CAR-MUC1 are examined for antitumor properties by assaying for percentage of residual tumor cells for tumor cells that express the target antigen at a high level. Twenty four hours after exposure of the CAR-MUC1 T cells to the tumor cells, those CAR-MUC1 T cells having high expression of the CAR are more effective than those CAR-MUC1 T cells having low expression of the CAR in eliminating the tumor cells that have high expression of the MUC1 antigen.

However, when comparing FIG. 11 vs. FIG. 12, the difference is not so significant between the efficiency of the low-expressing and high-expressing CAR-MUC1 T cells in target cells that have high expression of the target antigen. This indicates that the increase in expression of CARs on effector cells has an effect particularly on tumor cells that have low expression of the target antigen.

Figure 13:
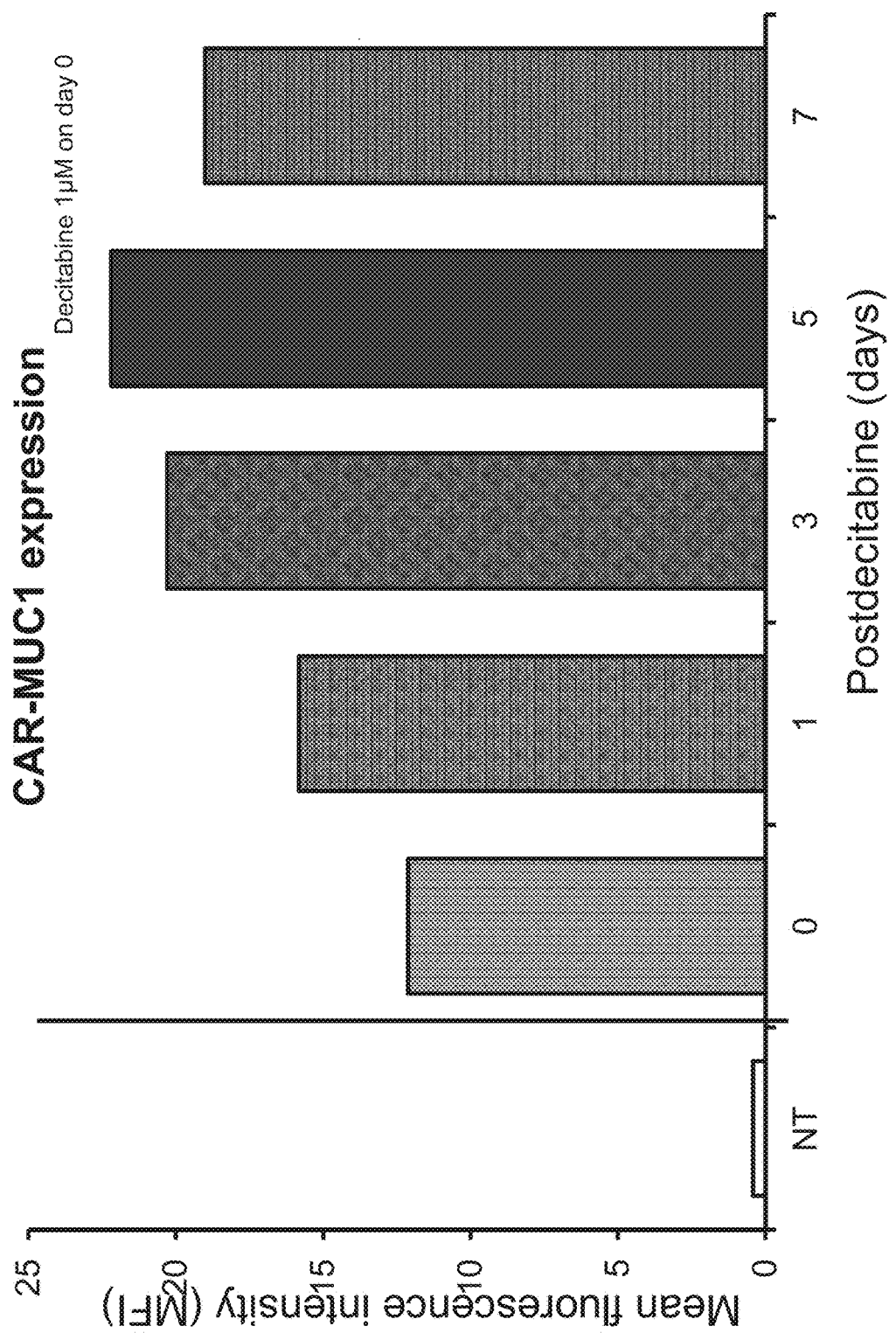
FIG. 13 demonstrates that decitabine enhances CAR expression on modified-T cells.

FIG. 13 demonstrates that decitabine enhances CAR expression on modified-T cells. It is illustrated therein that one can modulate the intensity of CAR-MUC1 expression on effector cells when the effector cells are cultured with decitabine. After one day, and certainly after several days, there is an increase in expression of the CAR-MUC1 on the cells.

Figure 14:
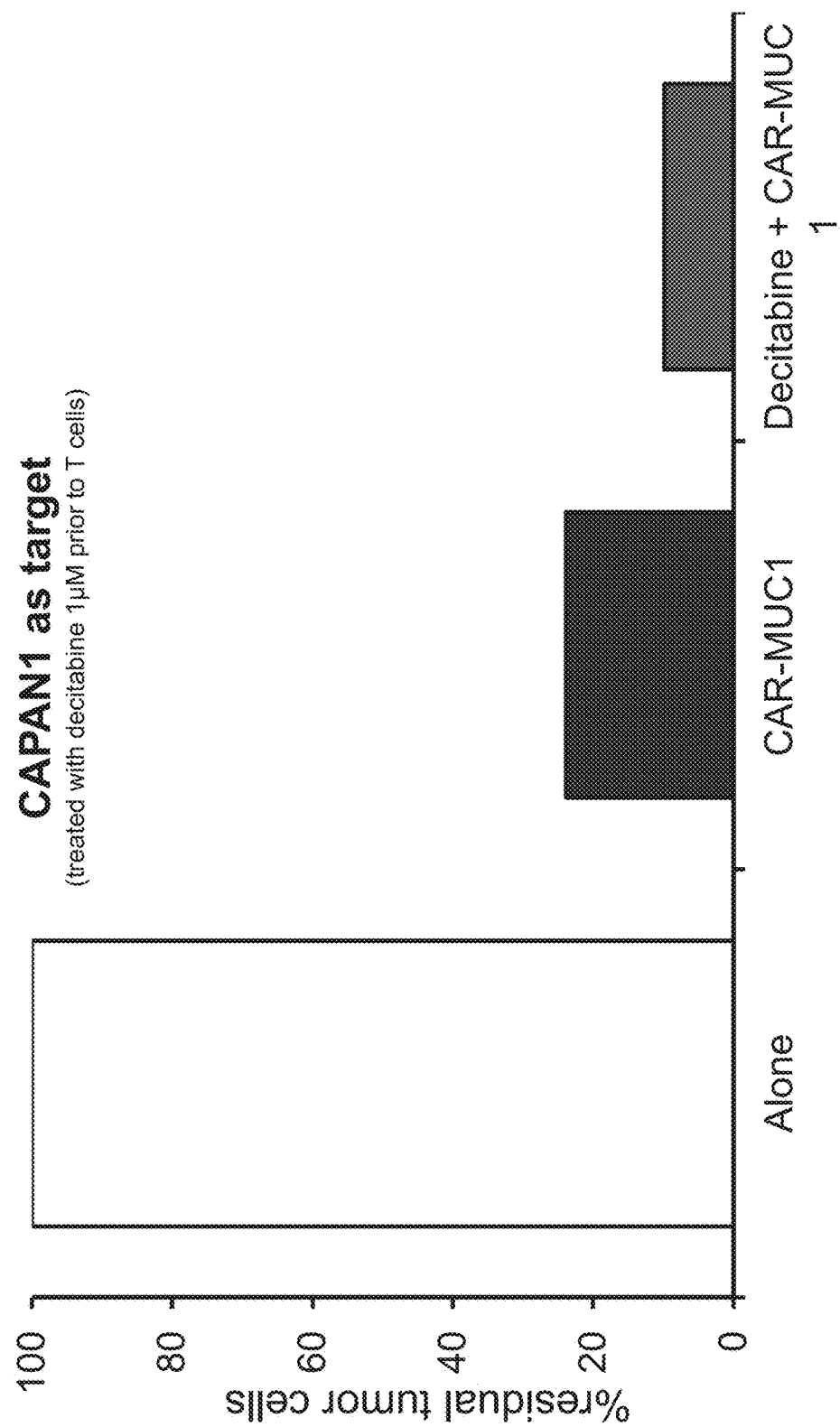
FIG. 14 shows that decitabine enhances antitumor effects of CAR-MUC1 T-cells.

FIG. 14 shows that decitabine enhances antitumor effects of CAR-MUC1 T-cells. As illustrated, there is an antitumor effect when comparing CAR-MUC1 T cells alone compared to the control, which results in about 80% tumor destruction. However, when the CAR-MUC1 T cells are combined with decitabine, there is increased potency by more than half than what is seen with the CAR-MUC1 T cells alone. Therefore, combination of decitabine and CAR-MUC1 T-cells increased the antitumor effect.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of enhancing potency of immune cells that express at least one therapeutic protein, comprising contacting the immune cells with an effective amount of DNA methyl transferase (DNMT) inhibitor for a time sufficient for expression of said therapeutic protein to increase, as compared to said immune cells not contacted with a mitogen, said DNMT inhibitor, wherein said immune cells are T cells, NK cells, dendritic cells, or a mixture thereof, wherein said therapeutic protein is a chimeric antigen receptor (CAR).

2. The method of claim 1, wherein said DNMT inhibitor is 5-azacytidine, decitabine, zebularine, SGI-110, SGI-1036, RG108, caffeic acid purum, chlorogenic acid, epigallocatechin galiate, procainamide hydrochloride, MG98, or a combination thereof.

3. The method of claim 2, wherein said 5-azacytidine is VIDAZA®.

4. The method of claim 1, wherein said immune cells are T cells.

5. The method of claim 4, wherein said T cells are CD4+ T cells, CD8+ T cells, or Treg cells.

6. The method of claim 1, wherein said contacting is performed in vitro.

7. The method of claim 1, wherein said contacting is performed in vivo in an individual comprising the immune cells.

8. The method of claim 1, wherein said immune cells and said DNMT inhibitor are administered to said individual separately.

9. The method of claim 1, wherein DNMT inhibitor, and said immune cells, are administered to the individual in separate pharmaceutical formulations.

10. The method of claim 1, wherein DNMT inhibitor, and said immune cells, are administered to the individual in the same pharmaceutical formulation.

11. The method of claim 1, wherein expression of said therapeutic protein in said immune cells is controlled by a promoter repressor region, at least a portion of the sequence of which is methylated, and wherein said methylation results in enhanced expression of said therapeutic protein.

12. The method of claim 1, wherein the CAR comprises at least one extracellular antigen-binding domain and at least one intracellular signaling domain.

13. The method of claim 1, wherein said immune cells are autologous to a recipient of said immune cells.

14. The method of claim 1, wherein said immune cells are allogeneic to a recipient of said immune cells.

15. The method of claim 1, wherein the immune cells comprise two or more different therapeutic proteins.

* * * * *